US008912348B2

(12) United States Patent
Tanaka

(10) Patent No.: US 8,912,348 B2
(45) Date of Patent: Dec. 16, 2014

(54) TETRAHYDROPYRANYL COMPOUND AND METHOD FOR PRODUCING THE TETRAHYDROPYRANYL COMPOUND

(75) Inventor: Yuuji Tanaka, Shizuoka (JP)

(73) Assignee: Ricoh Company, Ltd., Tokyo (JP)

( * ) Notice: Subject to any disclaimer, the term of this patent is extended or adjusted under 35 U.S.C. 154(b) by 409 days.

(21) Appl. No.: 13/390,534

(22) PCT Filed: Jun. 14, 2011

(86) PCT No.: PCT/JP2011/063995
§ 371 (c)(1),
(2), (4) Date: Feb. 15, 2012

(87) PCT Pub. No.: WO2011/158950
PCT Pub. Date: Dec. 22, 2011

(65) Prior Publication Data
US 2012/0142948 A1    Jun. 7, 2012

(30) Foreign Application Priority Data

Jun. 14, 2010   (JP) .................................. 2010-135428
Jun. 6, 2011    (JP) .................................. 2011-126568

(51) Int. Cl.
*C07D 315/00*    (2006.01)
*C07D 309/12*    (2006.01)

(52) U.S. Cl.
CPC .................................... *C07D 309/12* (2013.01)
USPC ......................................................... 549/415

(58) Field of Classification Search
CPC ............................ C07D 315/00; C07D 309/12
USPC ......................................................... 549/415
See application file for complete search history.

(56) References Cited

FOREIGN PATENT DOCUMENTS

| JP | 58 159536 | 9/1983 |
|----|-----------|--------|
| JP | 62 30255 | 2/1987 |
| JP | 63 225660 | 9/1988 |
| JP | 2001-166509 A | 6/2001 |
| JP | 2006 84711 | 3/2006 |
| JP | 2007 3929 | 1/2007 |
| JP | 2007 86366 | 4/2007 |
| JP | 2008 203640 | 9/2008 |
| JP | 2011 74050 | 4/2011 |

OTHER PUBLICATIONS

Extended European Search Report issued Apr. 15, 2013 in Patent Application No. 11795852.0.
International Search Report Issued Jul. 12, 2011 in PCT/JP11/63995 Filed Jun. 14, 2011.

*Primary Examiner* — T. Victor Oh
(74) *Attorney, Agent, or Firm* — Oblon, Spivak, McClelland, Maier & Neustadt, L.L.P.

(57) ABSTRACT

To provide a tetrahydropyranyl compound represented by General Formula (1) below: General Formula (1) where X denotes any one of a substituted or unsubstituted alkyl group, an oxygen atom, and a substituted or unsubstituted aromatic hydrocarbon group, $R_1, R_2, R_3, R_4, R_5$ and $R_6$ each denote any one of a hydrogen atom, a methyl group and an ethyl group, and n denotes an integer of 1 to 4.

(1)
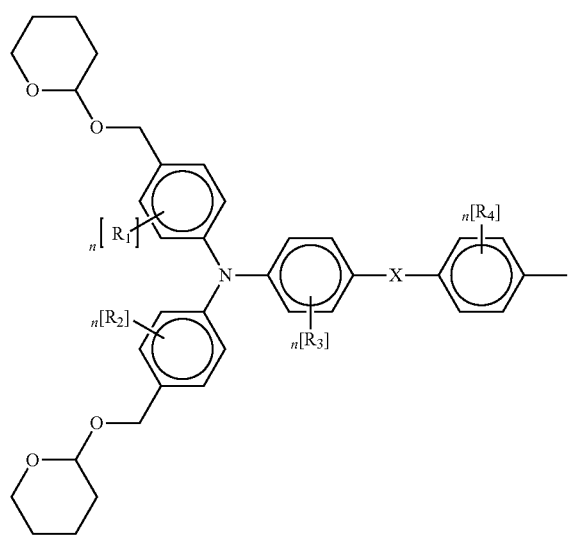
-continued
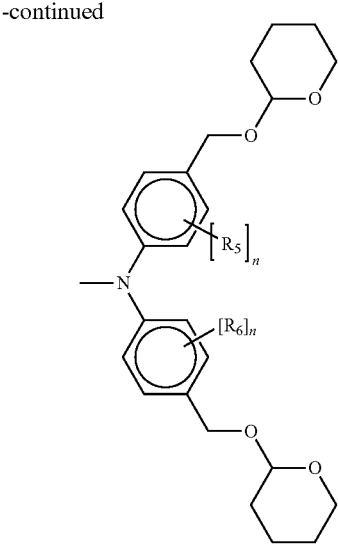
19 Claims, 8 Drawing Sheets

TETRAHYDROPYRANYL COMPOUND AND METHOD FOR PRODUCING THE TETRAHYDROPYRANYL COMPOUND

TECHNICAL FIELD

The present invention relates to a new tetrahydropyranyl compound useful for an organic photoconducting material, and a method for producing the tetrahydropyranyl compound.

The present invention also relates to a new tetrahydropyranyl compound useful as an organic charge transport material, a photoconducting material, etc., and a method for producing the tetrahydropyranyl compound.

The present invention further relates to an electronic element and an electronic component which use the new tetrahydropyranyl compound as an organic semiconductor material, examples of which include an organic electrophotographic photoconductor, an organic EL device, an organic TFT and an organic solar battery.

Specifically, the new tetrahydropyranyl compound includes, in its molecule, a tetrahydropyranyl group and a structural unit having a charge transporting function (hole transporting property), and the new tetrahydropyranyl compound is superior in compatibility with polymer materials such as polycarbonates and other monomers and capable of exhibiting a favorable charge transporting property.

BACKGROUND ART

An organic semiconductor material having a charge transporting function is useful as a semiconductor film forming material for an organic device such as an organic electrophotographic photoconductor, organic EL device, organic TFT or organic solar battery.

As a method for allowing a resin to have such a charge transporting function, there is a typical method of dispersing a charge transport material in a resin used as a binder for formation of a functional film, etc. For example, this method is widely used for electrophotographic photoconductors.

In recent years, due to the reduction in the size of photoconductors necessitated by the reduction in the size of electrophotographic apparatuses or the increase in the speed of the electrophotographic apparatuses, securing quick responsivity and stability of the photoconductors has been a very important aim.

Examples of commercially available charge transport materials include 1,1-bis(p-diethylaminophenyl)-4,4-diphenyl-1,3-butadiene (refer to PTL 1), 5-[4-(N,N-di-p-tolylamino)benzylidene]-5H-dibenzo[a,d]cycloheptene (refer to PTL 2), 9-methylcarbazole-3-aldehyde 1,1-diphenylhydrazone, pyrene-1-aldehyde 1,1-diphenylhydrazone (refer to PTL 3), 4'-bis(4-methylphenyl)amino-α-phenylstilbene, N,N'-diphenyl-N,N'-bis(3-methylphenyl)-[1,1'-biphenyl]-4,4'-diamine and 9,9-dimethyl-2-(di-p-tolylamino)fluorene.

A general charge transport layer is a solid solution film of approximately 10 μm to approximately 30 μm in thickness, obtained by dispersing any such low-molecular charge transport material in a binder resin.

As the binder resin, a bisphenol polycarbonate resin, a polyarylate resin or a copolymer composed of such a resin and other resin is used in most electrophotographic photoconductors. However, these charge transport materials do not have responsivity which can sufficiently adapt to a higher processing speed expected soon.

NPL 1 shows guidelines on molecular design in relation to quick responsivity (high mobility) of such charge transport materials. Specifically, NPL 1 states that a phenylamine group (>N-phenyl) serves as a functional group, there is a clear correlation between the number of functional groups and the mobility, and the mobility increases as the number of functional groups in a molecule increases; the compound of the present invention, which realizes quick responsivity by including a large number of functional groups, conforms to what is reported in NPL 1 on this point.

Meanwhile, the following have been reported: use of a tetrahydropyranyl group yields superior solubility in solvent and superior compatibility with a binder resin such as a polycarbonate resin; and low crystallinity of a charge transport material itself yields superior stability of a coating film and a coating liquid (refer to PTL 4). However, in the case where a tetrahydropyranyl group is included and an asymmetric molecular structure is employed, a low-viscosity liquid substance is easily produced. The low-viscosity liquid substance is superior in coating stability but poorly compatible with binder resins such as polycarbonate resins and easily degrades in terms of fingerprint resistance when stored for a long period of time. Moreover, the low-viscosity liquid substance easily degrades in terms of chargeability.

CITATION LIST

Patent Literature

PTL 1 Japanese Patent Application Laid-Open (JP-A) No. 62-30255
PTL 2 JP-A No. 63-225660
PTL 3 JP-A No. 58-159536
PTL 4 JP-A No. 2008-203640

Non Patent Literature

NPL 1 Denshi Shashin Gakkaishi (Electrophotography), 25 (3), 16 (1986)

SUMMARY OF INVENTION

Technical Problem

The present invention is designed in light of the above-mentioned related art and aimed at providing a new tetrahydropyranyl compound which is superior in compatibility with polymer materials such as polycarbonates and other monomers and capable of exhibiting a favorable charge transporting property, and which includes, in its molecule, a tetrahydropyranyl group and a structural unit having a charge transporting function (hole transporting property); and a method for producing the tetrahydropyranyl compound.

Solution to Problem

As a result of carrying out earnest examinations, the present inventors have found that a tetrahydropyranyl compound, capable of solving the above-mentioned problems, can be obtained by introducing a tetrahydropyranyl group into a compound with a charge transporting function, that has in its molecule a main backbone structure in which two triphenylamine structures are linked by a specific linking group.

It has been found that since the compound of the present invention includes a tetrahydropyranyl group and has a completely symmetric molecular structure, the compound easily becomes an amorphous or highly viscous liquid substance. Thus, the compound is superior in terms of solubility in a solvent, compatibility with a binder resin and stability of a coating film and a coating liquid, thereby having excellent properties.

The present invention is based upon the above-mentioned findings of the present inventors, and means for solving the problems are as follows.

<1> A tetrahydropyranyl compound represented by General Formula (1) below:

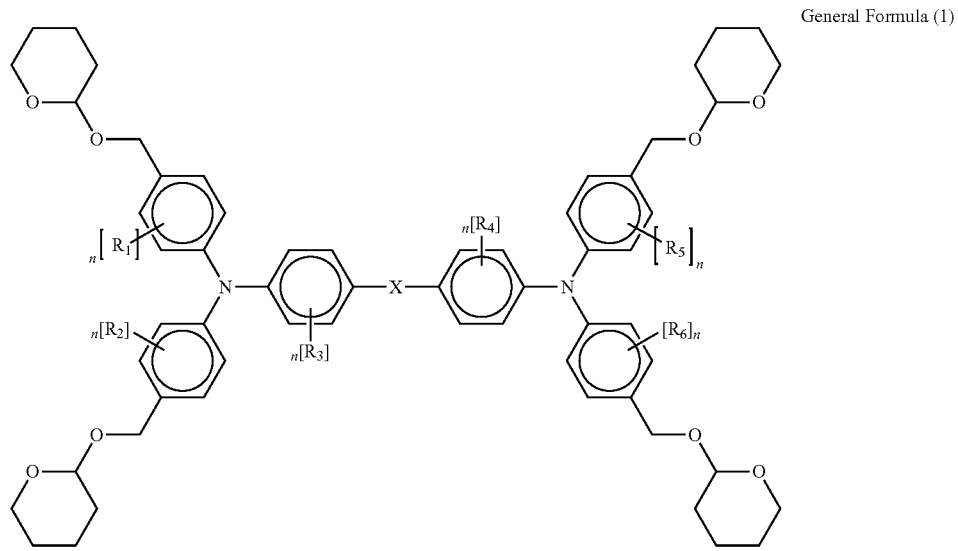

General Formula (1)

where X denotes any one of a substituted or unsubstituted alkyl group, an oxygen atom, and a substituted or unsubstituted aromatic hydrocarbon group, $R_1$, $R_2$, $R_3$, $R_4$, $R_5$ and $R_6$ each denote any one of a hydrogen atom, a methyl group and an ethyl group, and n denotes an integer of 1 to 4.

<2> A method for producing a tetrahydropyranyl compound represented by General Formula (1) below, including: reacting together a methylol compound represented by General Formula (2) below and 3,4-dihydro-2H-pyran represented by General Formula (3) below:

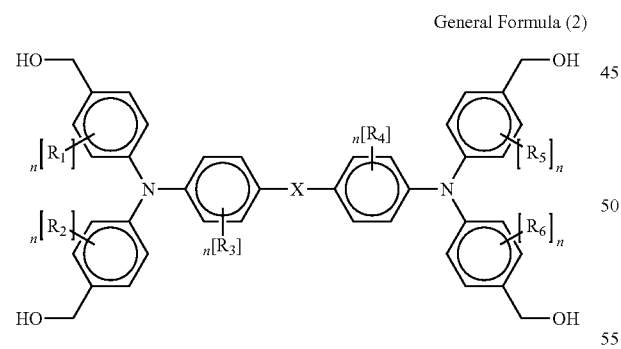

General Formula (2)

where X denotes any one of a substituted or unsubstituted alkyl group, an oxygen atom, and a substituted or unsubstituted aromatic hydrocarbon group, $R_1$, $R_2$, $R_3$, $R_4$, $R_5$ and $R_6$ each denote any one of a hydrogen atom, a methyl group and an ethyl group, and n denotes an integer of 1 to 4,

General Formula (3)

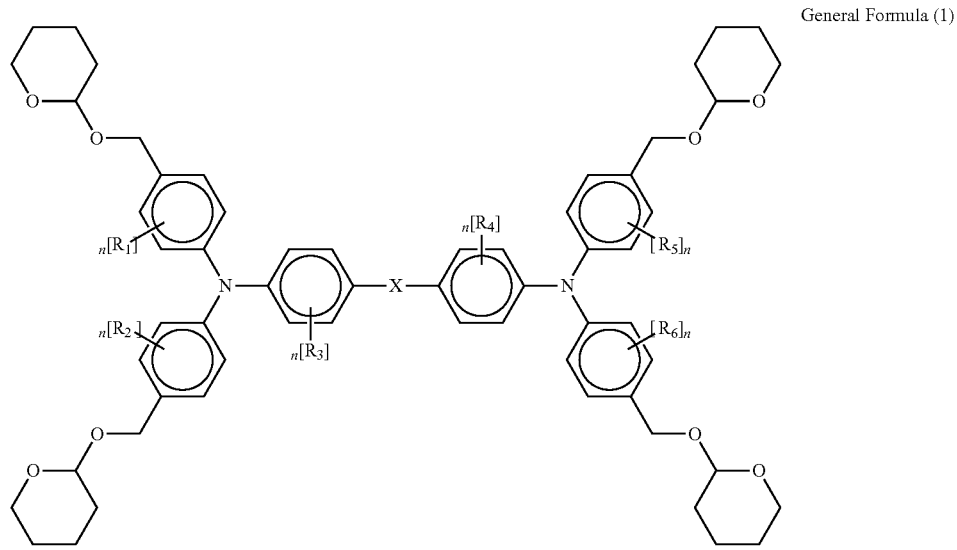

General Formula (1)

where X denotes any one of a substituted or unsubstituted alkyl group, an oxygen atom, and a substituted or unsubstituted aromatic hydrocarbon group, $R_1$, $R_2$, $R_3$, $R_4$, $R_5$ and $R_6$ each denote any one of a hydrogen atom, a methyl group and an ethyl group, and n denotes an integer of 1 to 4.

<3> A method for producing a tetrahydropyranyl compound represented by General Formula (1) below, including: reacting together an amine compound represented by General Formula (4) below and a bromo compound represented by General Formula (5) below:

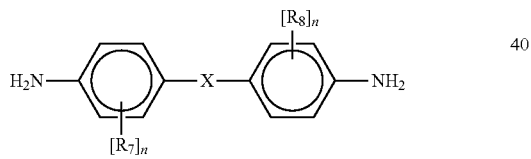

General Formula (4)

where X denotes any one of —O—, —CH$_2$—, —CH$_2$CH$_2$—, —C(CH$_3$)$_2$-Ph-C(CH$_3$)$_2$— and —C(CH$_3$)$_2$—, $R_7$ and $R_8$ each denote any one of a hydrogen atom, a methyl group and an ethyl group, and n denotes an integer of 1 to 4,

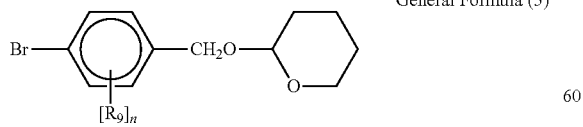

General Formula (5)

where $R_9$ denotes any one of a hydrogen atom, a methyl group and an ethyl group, and n denotes an integer of 1 to 4,

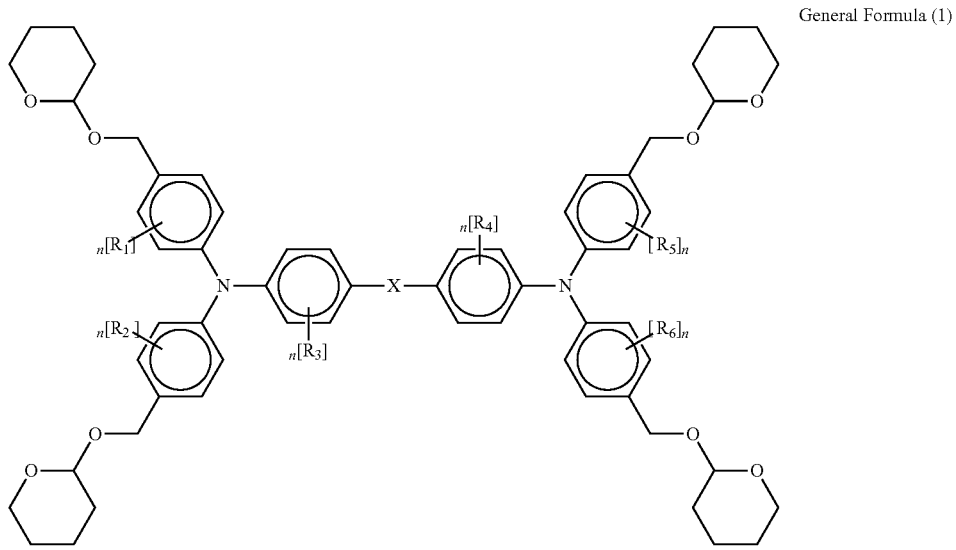

General Formula (1)

where X denotes any one of a substituted or unsubstituted alkyl group, an oxygen atom, and a substituted or unsubstituted aromatic hydrocarbon group, $R_1$, $R_2$, $R_3$, $R_4$, $R_5$ and $R_6$ each denote any one of a hydrogen atom, a methyl group and an ethyl group, and n denotes an integer of 1 to 4.

<4> The tetrahydropyranyl compound according to <1>, wherein the General Formula (1) is represented by General Formula (6) below:

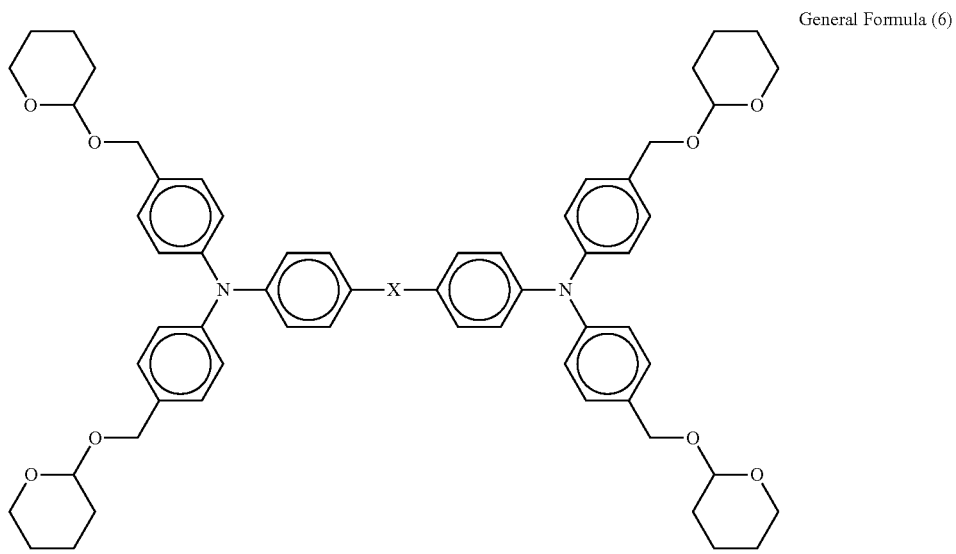

General Formula (6)

where X denotes any one of —O—, —$CH_2$—, —$CH_2CH_2$—, —$C(CH_3)_2$-Ph-$C(CH_3)_2$— and —$C(CH_3)_2$—.

<5> A method for producing a tetrahydropyranyl compound represented by General Formula (6) below, including: reacting together a methylol compound represented by General Formula (7) below and 3,4-dihydro-2H-pyran represented by General Formula (3) below:

General Formula (7)

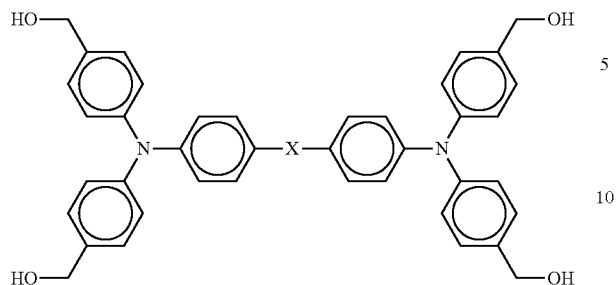

where X denotes any one of —O—, —CH₂—, —CH₂CH₂—, —C(CH₃)₂-Ph-C(CH₃)₂— and —C(CH₃)₂—, General Formula (3)

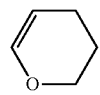

General Formula (6)

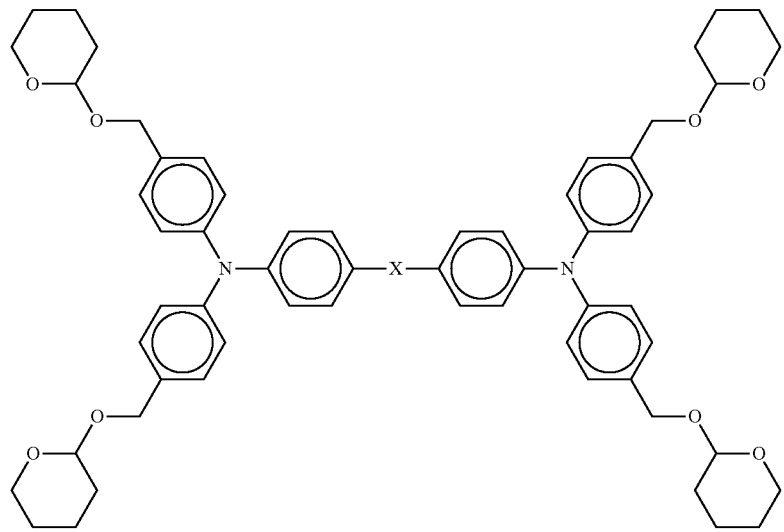

where X denotes any one of —O—, —CH₂—, —CH₂CH₂—, —C(CH₃)₂-Ph-C(CH₃)₂— and —C(CH₃)₂—.

<6> A method for producing a tetrahydropyranyl compound represented by General Formula (6) below, including: reacting together an amine compound represented by General Formula (8) below and a bromo compound represented by General Formula (9) below:

General Formula (8)

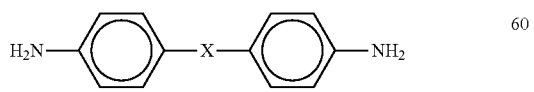

where X denotes any one of —O—, —CH₂—, —CH₂CH₂—, —C(CH₃)₂-Ph-C(CH₃)₂— and —C(CH₃)₂—,

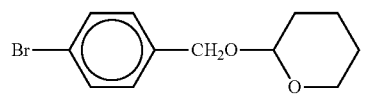

General Formula (9)

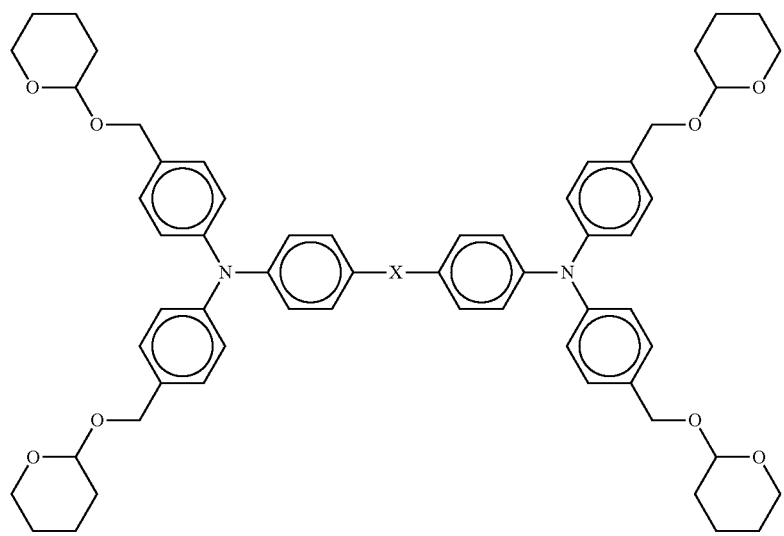

General Formula (6)

where X denotes any one of —O—, —CH$_2$—, —CH$_2$CH$_2$—, —C(CH$_3$)$_2$-Ph-C(CH$_3$)$_2$— and —C(CH$_3$)$_2$—.

Advantageous Effects of Invention

A new tetrahydropyranyl compound of the present invention represented by General Formula (1) or (6) includes a tetrahydropyranyl group and a charge transporting site and is superior in film forming property and compatibility with polymer materials such as polycarbonates and other monomers.

Also, the following excellent effects are produced: it is possible to synthesize a desired tetrahydropyranyl compound with ease by reacting together 3,4-dihydro-2H-pyran represented by General Formula (3) above and a methylol compound represented by General Formula (2) or (7) above that are useful as raw materials for producing the tetrahydropyranyl compound of the present invention; further, it is possible to synthesize a desired tetrahydropyranyl compound with ease by reacting together an amine compound represented by General Formula (4) or (8) above and a bromo compound represented by General Formula (5) or (9) above as raw materials for producing the tetrahydropyranyl compound of the present invention.

DESCRIPTION OF EMBODIMENTS

Figure 1:
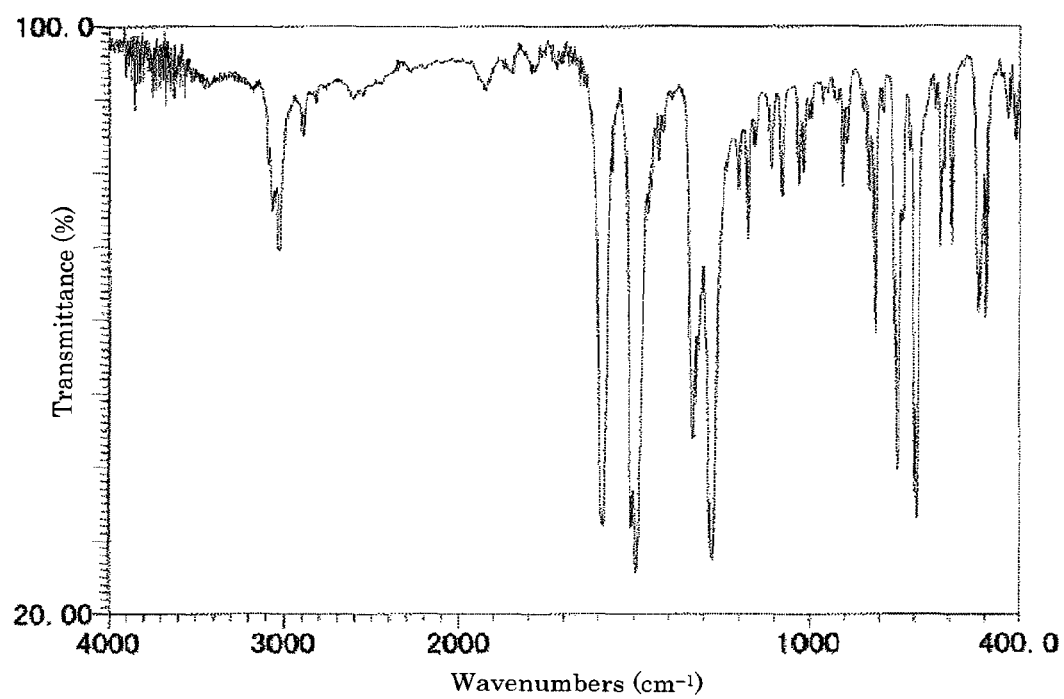
FIG. 1 is a diagram showing an infrared absorption spectrum of a compound obtained in Synthesis Example 1 (KBr tablet method), where the horizontal axis denotes wavenumbers (cm$^{-1}$), and the vertical axis denotes transmittance (%).

A tetrahydropyranyl compound of the present invention is represented by General Formula (1) below.

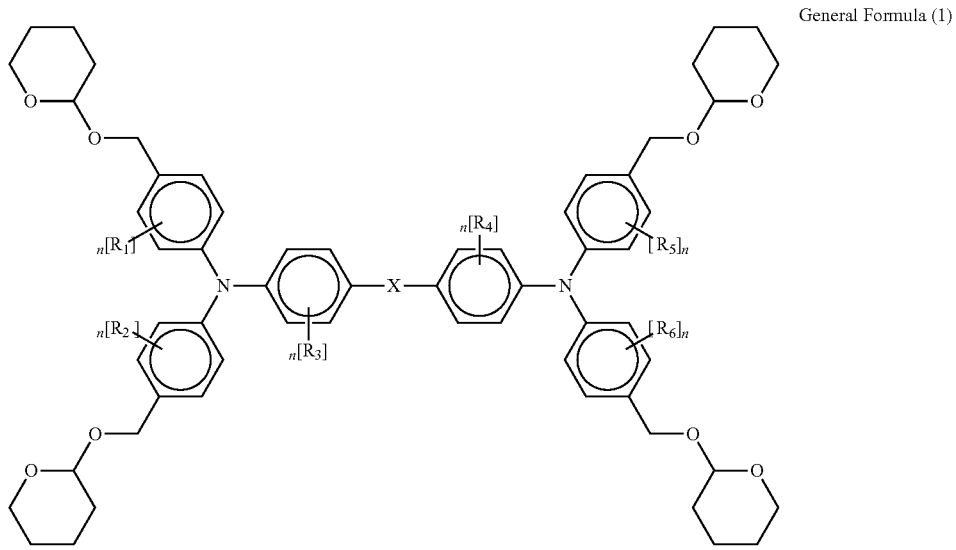

General Formula (1)

In General Formula (1), X denotes any one of a substituted or unsubstituted alkyl group, an oxygen atom, and a substituted or unsubstituted aromatic hydrocarbon group, $R_1$, $R_2$, $R_3$, $R_4$, $R_5$ and $R_6$ each denote any one of a hydrogen atom, a methyl group and an ethyl group, and n denotes an integer of 1 to 4.

X preferably denotes any one of —O—, —CH$_2$—, —CH$_2$CH$_2$—, —C(CH$_3$)$_2$-Ph-C(CH$_3$)$_2$— and —C(CH$_3$)$_2$—.

The tetrahydropyranyl compound represented by General Formula (1) above is preferably a compound represented by General Formula (6) below.

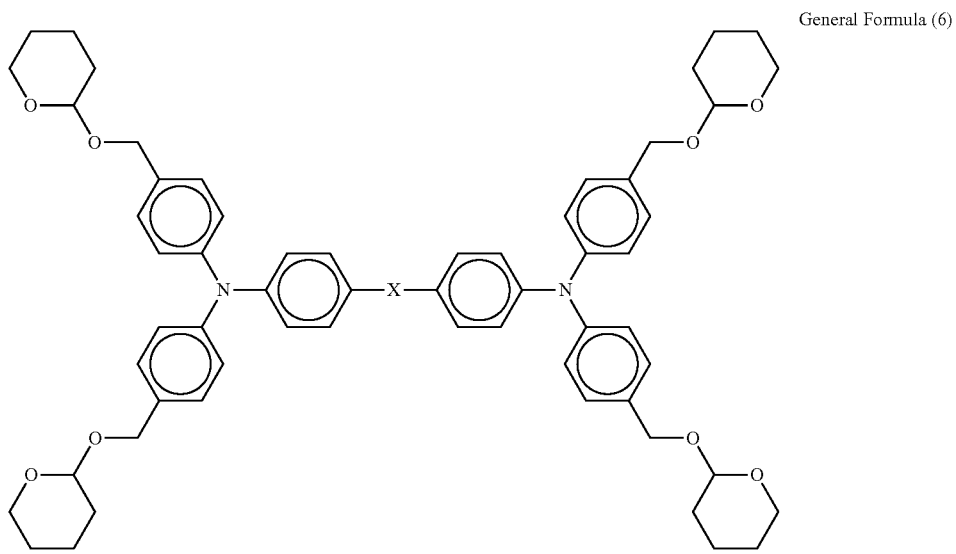

General Formula (6)

In General Formula (6), X denotes any one of —O—, —CH$_2$—, —CH$_2$CH$_2$—, —C(CH$_3$)$_2$-Ph-C(CH$_3$)$_2$— and —C(CH$_3$)$_2$—.

The following shows specific examples of the tetrahydropyranyl compound of the present invention represented by General Formula (1) above; note that the present invention is not limited to compounds shown as the examples.

Compound No. 1
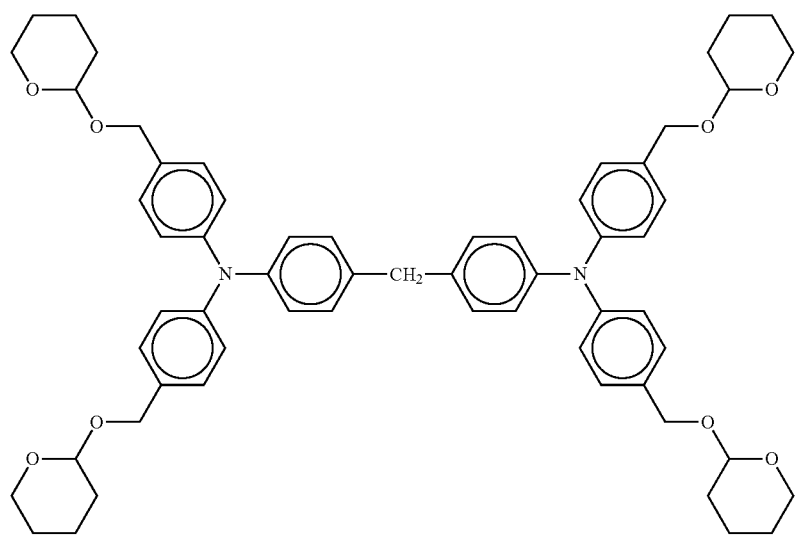
Compound No. 2
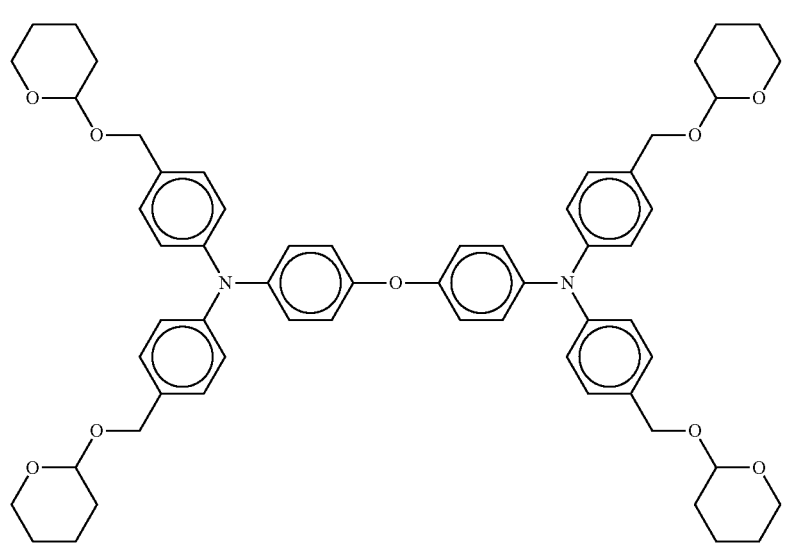
Compound No. 3
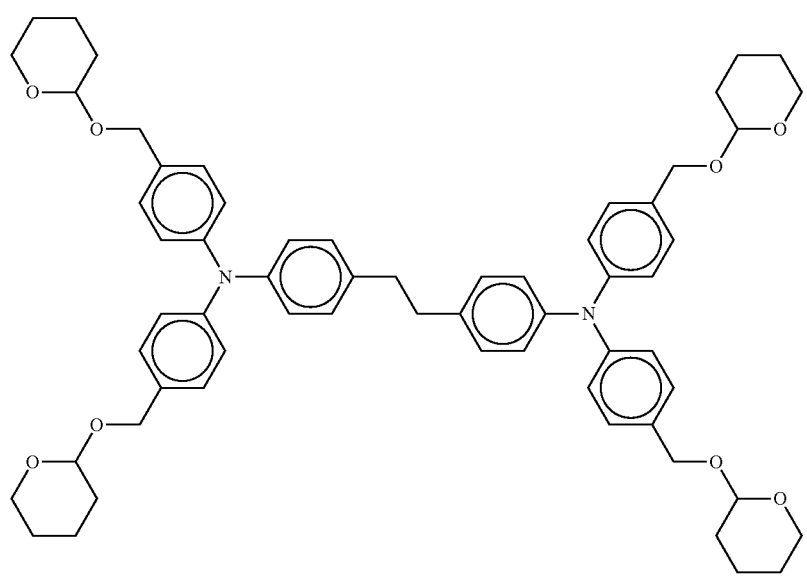

-continued
Compound No.4
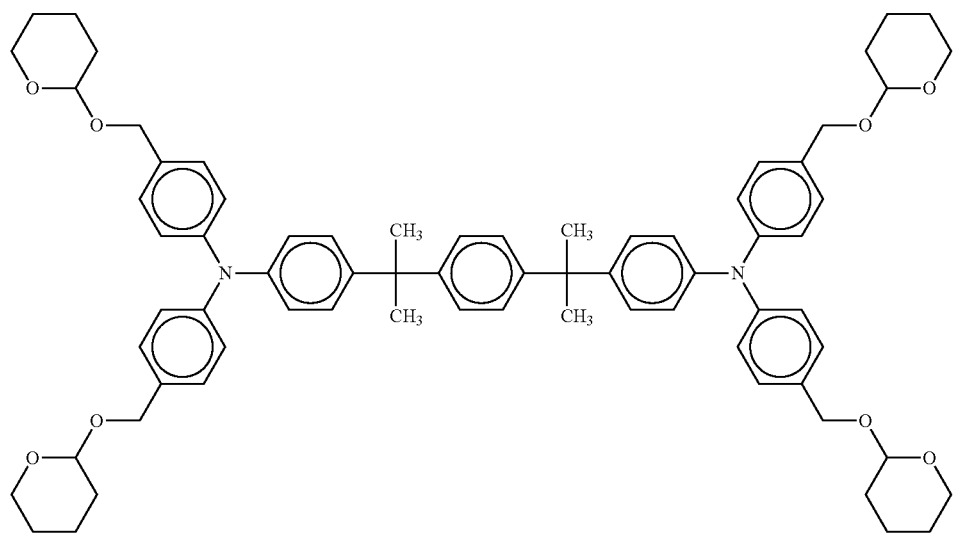
Compound No. 5
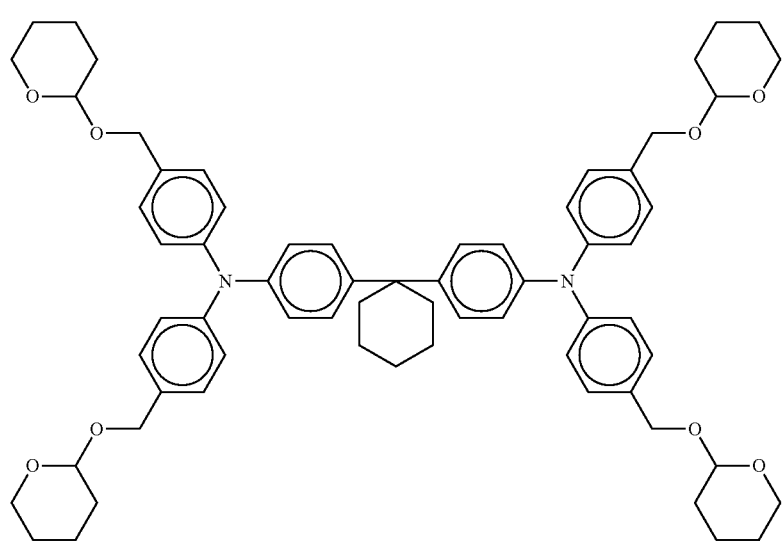
Compound No. 6
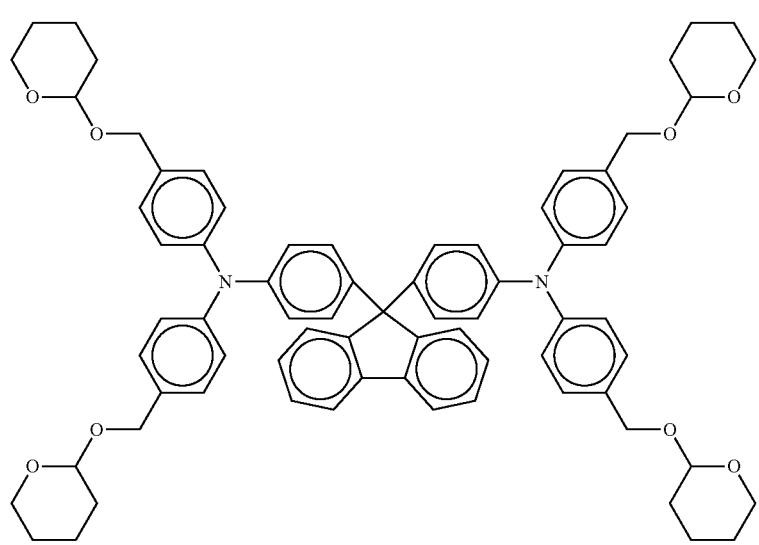

-continued
Compound No.7
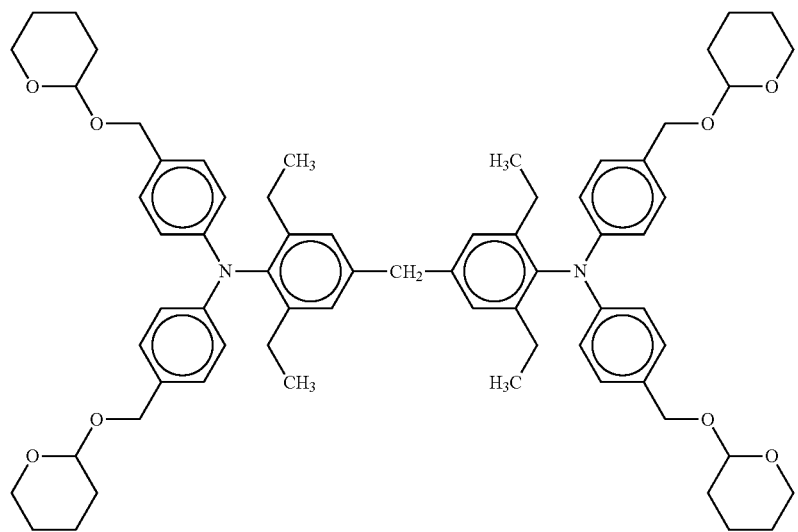
Compound No. 8
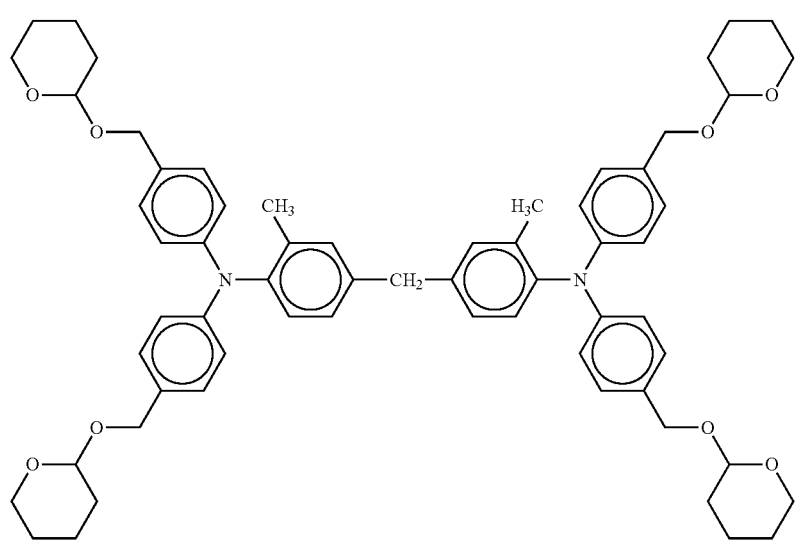
Compound No. 9
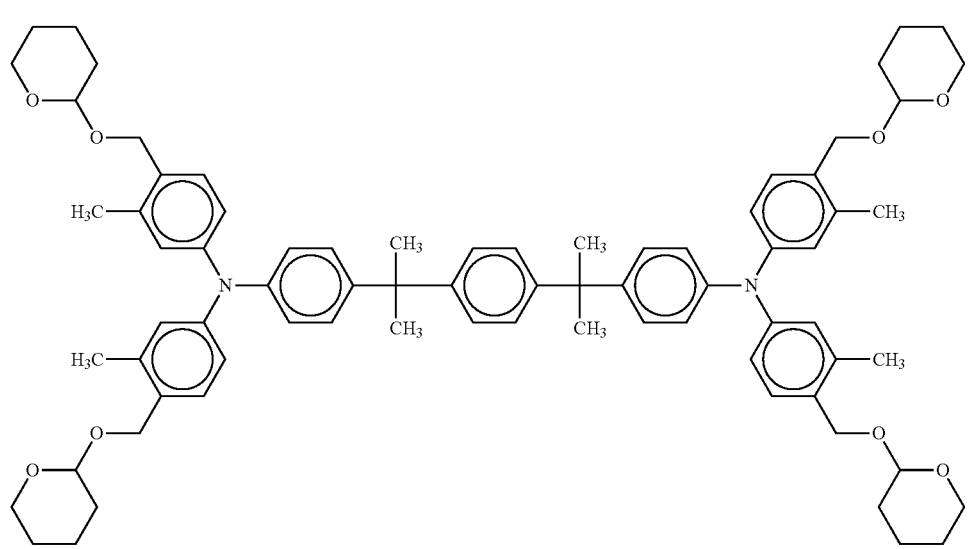

Compound No. 10
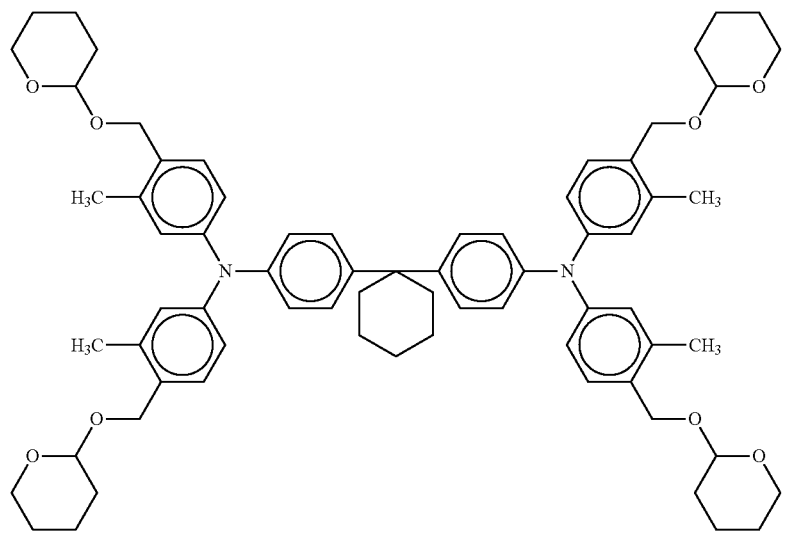
Compound No. 11
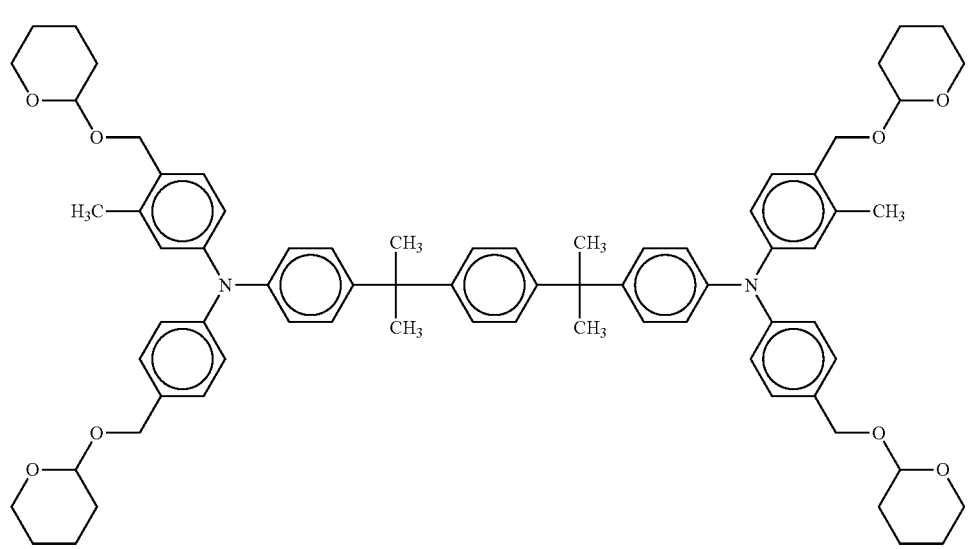
Compound No. 12
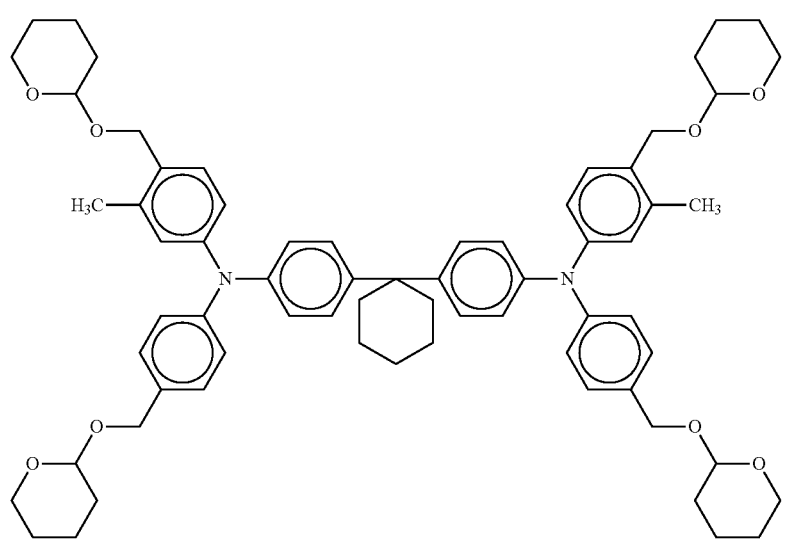

-continued
Compound No. 13
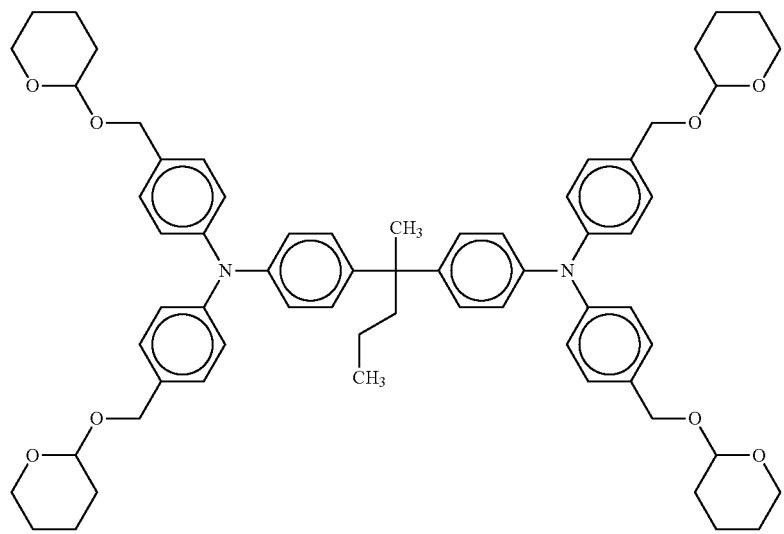
Compound No. 14
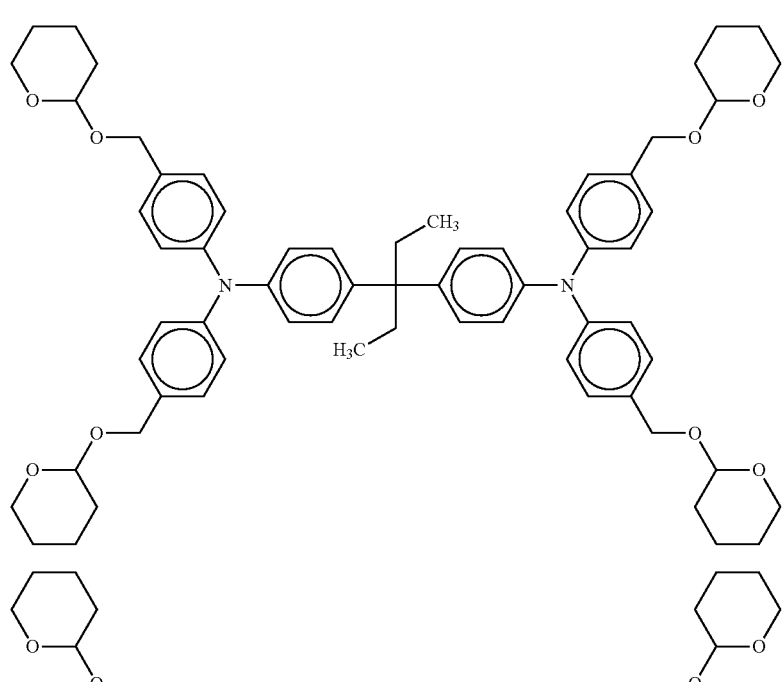
Compound No. 15
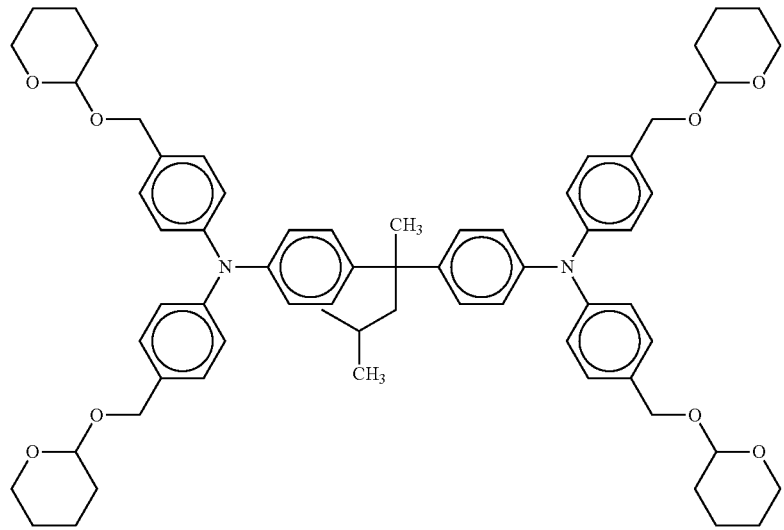

The tetrahydropyranyl compound of the present invention represented by General Formula (1) or (6) above is a new substance and can be synthesized by reacting together a methylol compound represented by General Formula (2) or (7) below and 3,4-dihydro-2H-pyran represented by General Formula (3) below.

General Formula (2)

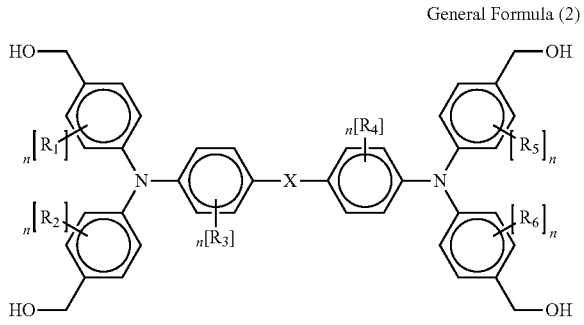

In General Formula (2), X denotes any one of a substituted or unsubstituted alkyl group, an oxygen atom, and a substituted or unsubstituted aromatic hydrocarbon group, R$_1$, R$_2$, R$_3$, R$_4$, R$_5$ and R$_6$ each denote any one of a hydrogen atom, a methyl group and an ethyl group, and n denotes an integer of 1 to 4.

General Formula (7)

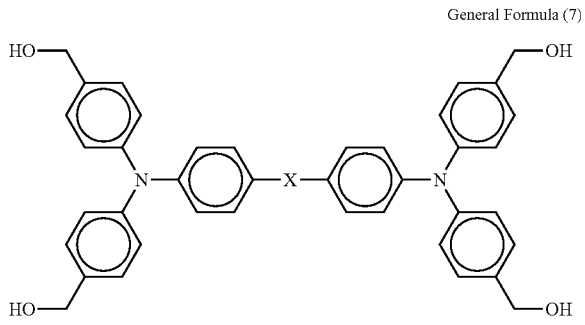

In General Formula (7), X denotes any one of —O—, —CH$_2$—, —CH$_2$CH$_2$—, —C(CH$_3$)$_2$-Ph-C(CH$_3$)$_2$— and —C(CH$_3$)$_2$—.

General Formula (3)

Also, the tetrahydropyranyl compound can be synthesized by reacting together an amine compound represented by General Formula (4) or (8) below and a bromo compound represented by General Formula (5) or (9) below.

General Formula (4)

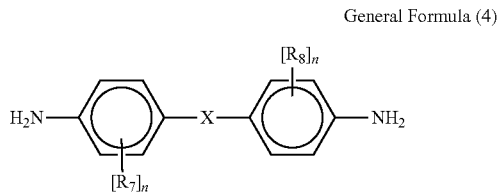

In General Formula (4), X denotes any one of —O—, —CH$_2$—, —CH$_2$CH$_2$—, —C(CH$_3$)$_2$-Ph-C(CH$_3$)$_2$— and —C(CH$_3$)$_2$—, R$_7$ and R$_8$ each denote any one of a hydrogen atom, a methyl group and an ethyl group, and n denotes an integer of 1 to 4.

General Formula (8)

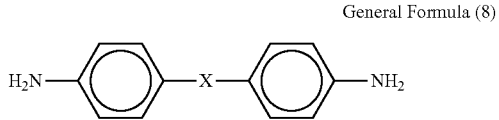

In General Formula (8), X denotes any one of —O—, —CH$_2$—, —CH$_2$CH$_2$—, —C(CH$_3$)$_2$-Ph-C(CH$_3$)$_2$— and —C(CH$_3$)$_2$—.

General Formula (5)

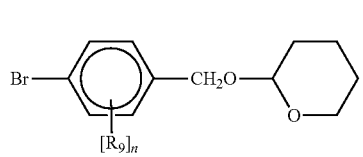

In General Formula (5), R$_9$ denotes any one of a hydrogen atom, a methyl group and an ethyl group, and n denotes an integer of 1 to 4.

General Formula (9)

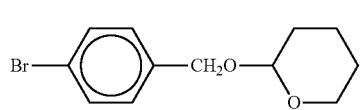

For example, a methylol compound for use in the present invention can be easily synthesized as follows: an aldehyde compound is synthesized in accordance with the procedure explained below, the obtained aldehyde compound is subjected to a reducing reaction with a reducing agent such as sodium borohydride to synthesize a methylol compound, and the obtained methylol compound is reacted with 3,4-dihydro-2H-pyran.

Examples of the amine compound include 4,4'-diaminodiphenylmethane, 9,9'-bis(4-aminophenyl)fluorene, 9,9'-bis(4-amino-3-methylphenyl)fluorene, 9,9'-bis(3-amino-4-hydroxyphenyl)fluorene, 9,9'-bis(4-amino-3-fluorophenyl)fluorene, 9,9'-bis(4-amino-3-chlorophenyl)fluorene, 1,1-bis(4-aminophenyl)cyclohexane, 4,4'-methylenebis(2-ethyl-6-methylaniline), α,α'-bis(4-aminophenyl)-1,4-diisopropylbenzene, 4,4'-methylenebis(2,6-diethylaniline), 4,4'-diamino-3,3'-dimethyldiphenylmethane, 2,2-bis(3-aminophenyl)hexafluoropropane, 4,4'-ethylenedianiline, 4,4'-diaminostilbene dihydrochloride, bis(4-amino-2,3-dichlorophenyl)methane, 4,4'-diamino-2,2'-dimethylbibenzyl, 4,4'-diaminobenzophenone, 4,4'-diaminodiphenyl ether, 1,4-bis(4-aminophenoxy)benzene, 1,3-bis(4-aminophenoxy)benzene and 1,3-bis(3-aminophenoxy)benzene.

<Synthesis of Aldehyde Compound>

The aldehyde compound can be synthesized by formylating a triphenylamine compound as a raw material, using a conventionally known method (e.g., the Vilsmeier reaction), as shown by the reaction formula below.

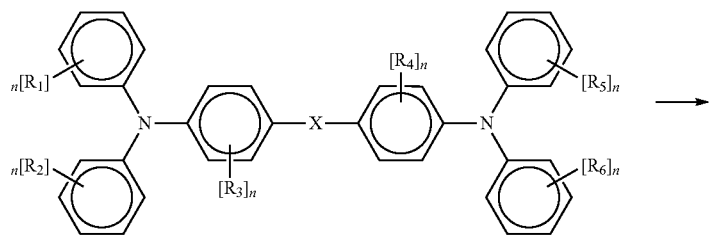

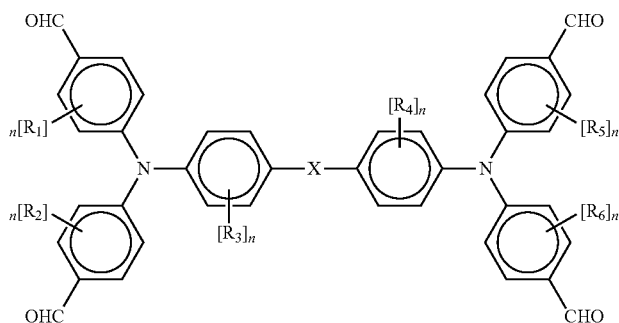

As a specific method for the formylation, a method using zinc chloride, phosphorus oxychloride and dimethyl formaldehyde is effective; note that the synthesis method for obtaining the aldehyde compound as an intermediate (a raw material for the tetrahydropyranyl compound) in the present invention is not limited to the foregoing method. Specific synthesis examples will later be stated in Examples.

<Synthesis of Methylol Compound>

The methylol compound can be synthesized by a conventionally known reducing method using an aldehyde compound as a raw material for production, as shown by the reaction formula below.

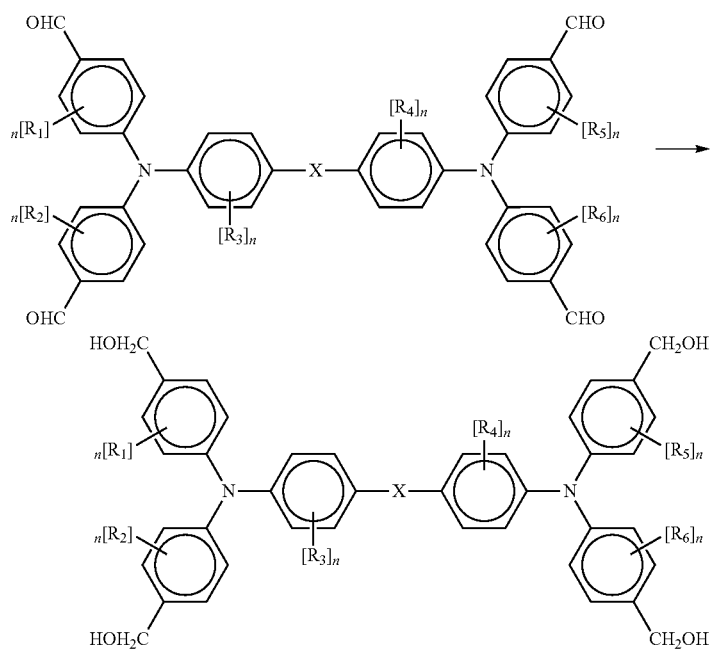

Specifically, as the reducing method, a method using sodium borohydride is effective; note that the synthesis method for obtaining the methylol compound as an intermediate (a raw material for the tetrahydropyranyl compound) in the present invention is not limited to the foregoing method. Specific synthesis examples will later be stated in Examples.

Since the tetrahydropyranyl compound of the present invention represented by General Formula (1) or (6) above has in its molecule a main backbone structure in which two triphenylamine structures are linked by a specific linking group, the tetrahydropyranyl compound has a charge transporting function in such a manner that the tetrahydropyranyl compound is low in crystallinity and superior in compatibility with polymer materials such as polycarbonates and other monomers.

EXAMPLES

The following explains the present invention in further detail, referring to Synthesis Examples and Examples; note that the present invention is not confined to these Examples. Hereinafter, the term "parts" denotes "parts by mass".

Synthesis Example 1 (Synthesis of an Aldehyde Compound (Raw Material) as an Intermediate for a Tetrahydropyranyl Compound No. 1 Shown as an Example)

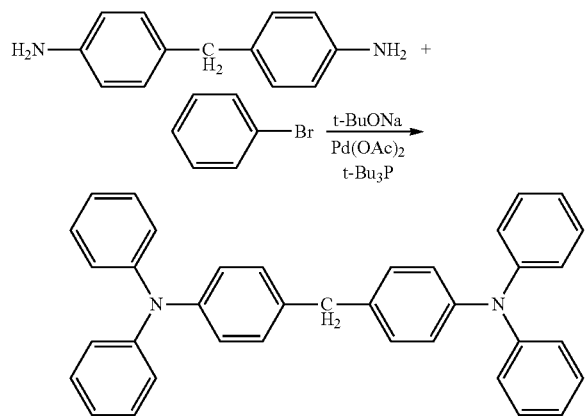

In a four-necked flask, 19.83 g of 4,4'-diaminodiphenylmethane, 69.08 g of bromobenzene, 2.24 g of palladium acetate, 46.13 g of tert-butoxysodium and 250 mL of o-xylene were placed.

In an argon gas atmosphere, the above ingredients were stirred at room temperature.

Dropwise addition of 8.09 g of tri-tert-butylphosphine was carried out.

Stirring was continued for 1 hour at 80° C. and 1 hour in a state of reflux.

The ingredients were diluted with toluene, which was followed by addition of magnesium sulfate, activated clay and silica gel, and then stirring was carried out.

The ingredients were filtered, washed and concentrated to obtain crystalline matter.

The crystalline matter was dispersed in methanol, which was followed by filtration, washing and drying, and an intended product was thus obtained (yield: 45.73 g, pale yellow powder).

A diagram showing an infrared absorption spectrum of the compound obtained in Synthesis Example 1 (KBr tablet method) is in FIG. 1.

Synthesis Example 2 (Synthesis of a Methylol Compound (Raw Material) as an Intermediate for a Tetrahydropyranyl Compound No. 1 Shown as an Example)

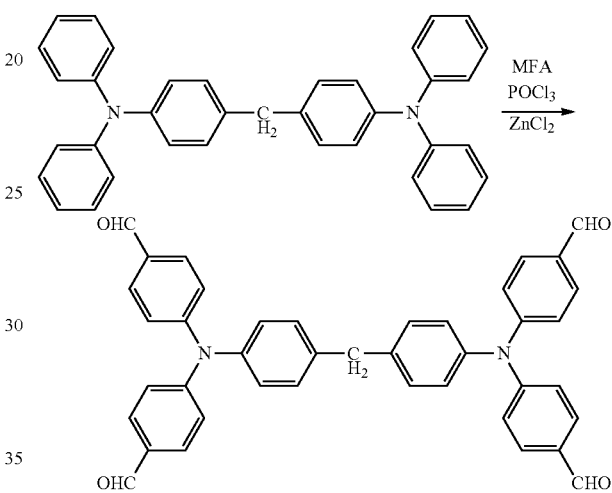

In a four-necked flask, 30.16 g of a raw material for an intermediate, 71.36 g of N-methylformanilide and 400 mL of o-dichlorobenzene were placed.

In an argon gas atmosphere, the above ingredients were stirred at room temperature.

Dropwise addition of 82.01 g of phosphorus oxychloride was carried out. The temperature was increased to 80° C., and the ingredients were stirred.

Dropwise addition of 32.71 g of zinc chloride was carried out.

The ingredients were stirred at 80° C. for approximately 10 hours, then stirring was continued at 120° C. for approximately 3 hours.

A potassium hydroxide aqueous solution was added so as to effect a hydrolytic reaction.

An extracting process with dichloromethane, a dehydrating process with magnesium sulfate, and an adsorbing process with activated clay were performed.

The ingredients were filtered, washed and concentrated to obtain crystalline matter.

A column cleanup with silica gel (toluene/ethyl acetate=8/2) was performed so as to effect isolation.

The obtained crystalline matter was recrystallized with methanol and ethyl acetate to obtain an intended product (yield: 27.80 g, yellow powder).

Figure 2:
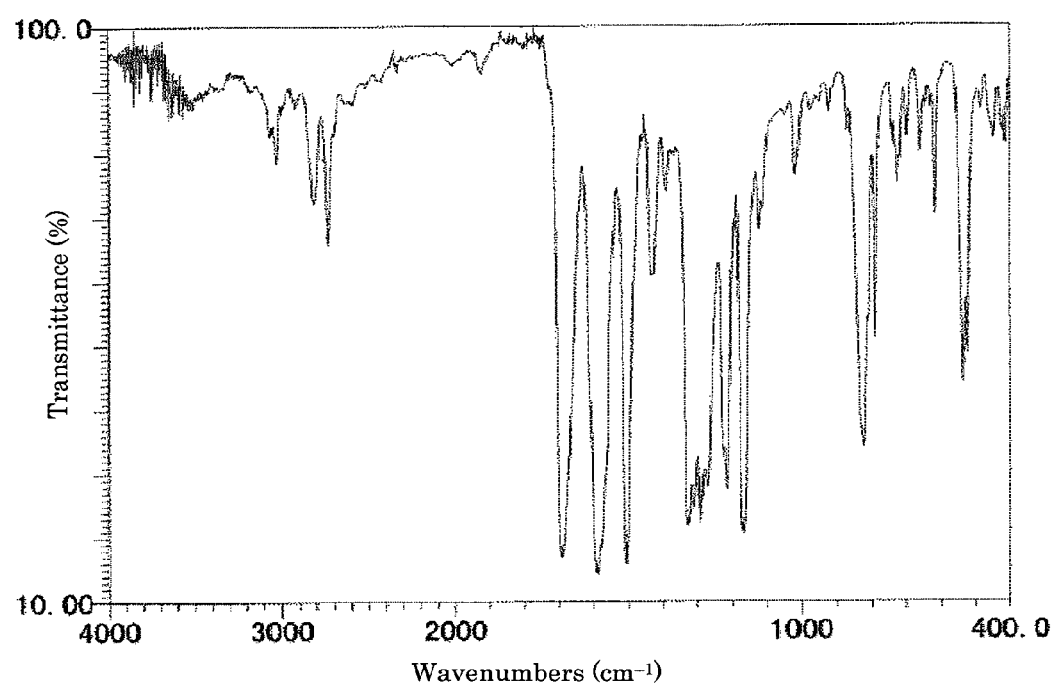
FIG. 2 is a diagram showing an infrared absorption spectrum of a compound obtained in Synthesis Example 2 (KBr tablet method), where the horizontal axis denotes wavenumbers (cm$^{-1}$), and the vertical axis denotes transmittance (%).

A diagram showing an infrared absorption spectrum of the compound obtained in Synthesis Example 2 (KBr tablet method) is in FIG. 2.

Synthesis Example 3 (Synthesis of a Methylol Compound Used as a Raw Material for Production of a Tetrahydropyranyl Compound No. 1 Shown as an Example)

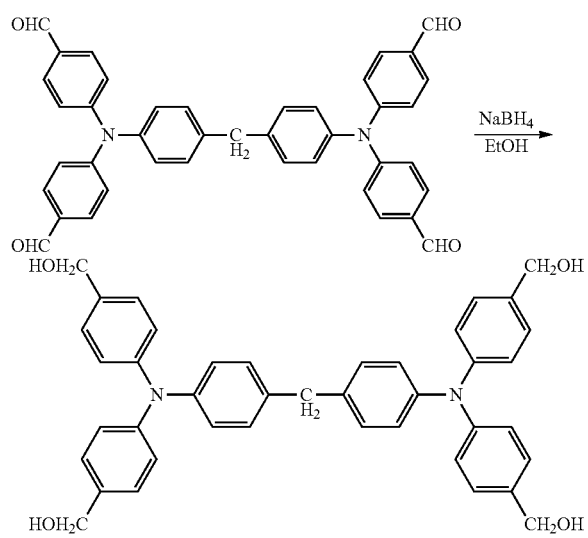

In a four-necked flask, 12.30 g of an aldehyde compound as an intermediate and 150 mL of ethanol were placed.

The ingredients were stirred at room temperature, 3.63 g of sodium borohydride was poured, and stirring was continued for 4 hours.

An extracting process with ethyl acetate, a dehydrating process with magnesium sulfate, and an adsorbing process with activated clay and silica gel were performed.

By filtrating, washing and concentrating the ingredients, an amorphous substance was obtained.

The amorphous substance was dispersed in n-hexane, which was followed by filtration, washing and drying, and an intended product was thus obtained (yield: 12.0 g, pale yellowish-white amorphous product).

Figure 3:
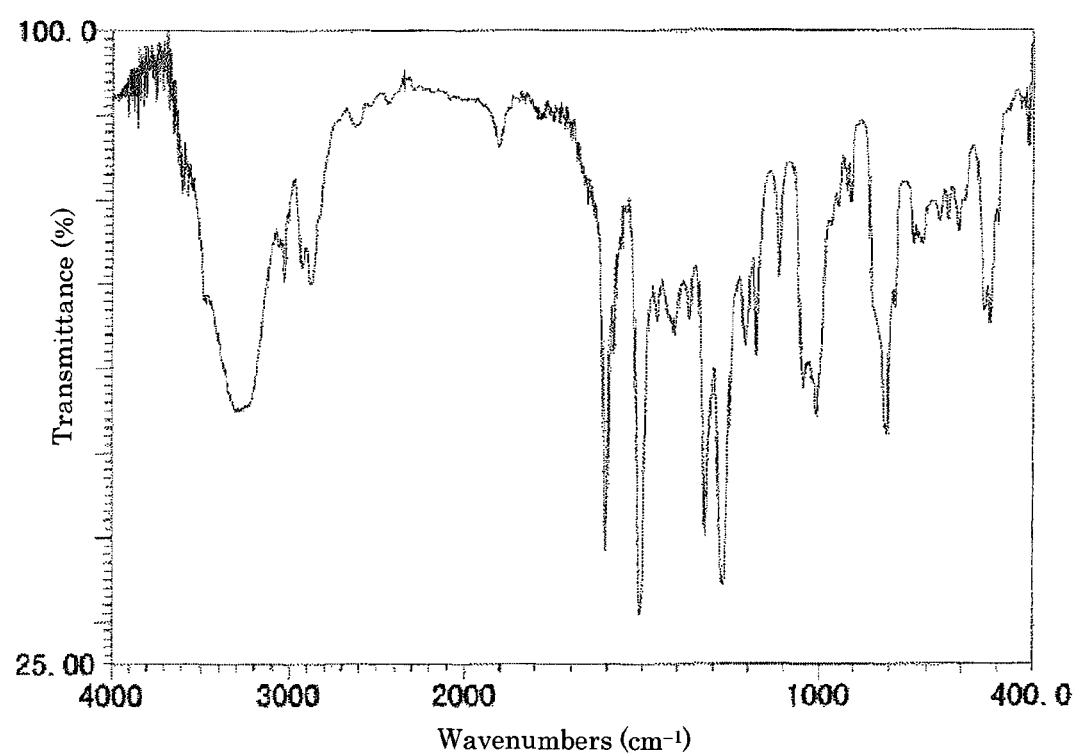
FIG. 3 is a diagram showing an infrared absorption spectrum of a compound obtained in Synthesis Example 3 (KBr tablet method), where the horizontal axis denotes wavenumbers (cm$^{-1}$), and the vertical axis denotes transmittance (%).

A diagram showing an infrared absorption spectrum of the methylol compound obtained in Synthesis Example 3 (KBr tablet method) is in FIG. 3.

Example 1

Synthesis Example 4 (Example 1: Synthesis of a Tetrahydropyranyl Compound No. 1 Shown as an Example)

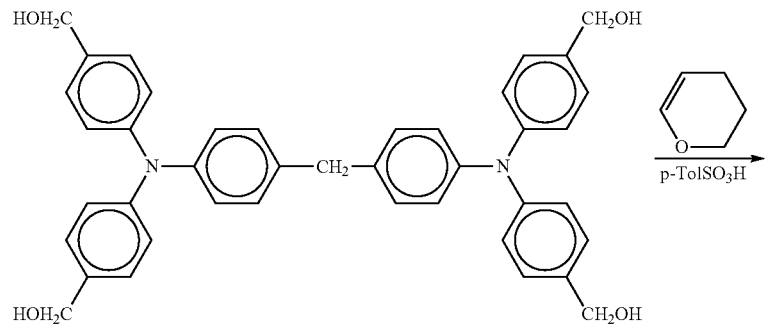

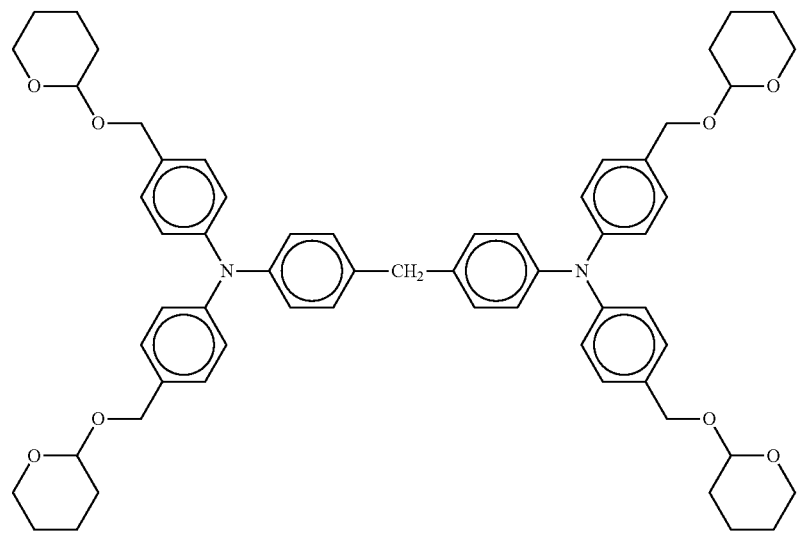

In a four-necked flask, 6.4 g of a methylol compound as an intermediate, 6.915 g of 3,4-dihydro-2H-pyran and 100 mL of tetrahydrofuran were placed.

The ingredients were stirred at 5° C., and 78 mg of p-toluenesulfonic acid was poured. Stirring was continued for 5 hours at room temperature.

An extracting process with ethyl acetate, a dehydrating process with magnesium sulfate, and an adsorbing process with activated clay and silica gel were performed.

By filtrating, washing and concentrating the ingredients, a yellow oily substance was obtained.

A column cleanup with silica gel (toluene/ethyl acetate=5/1) was performed so as to effect isolation, and an intended product was thus obtained (yield: 5.7 g, pale yellow oily matter).

Figure 4:
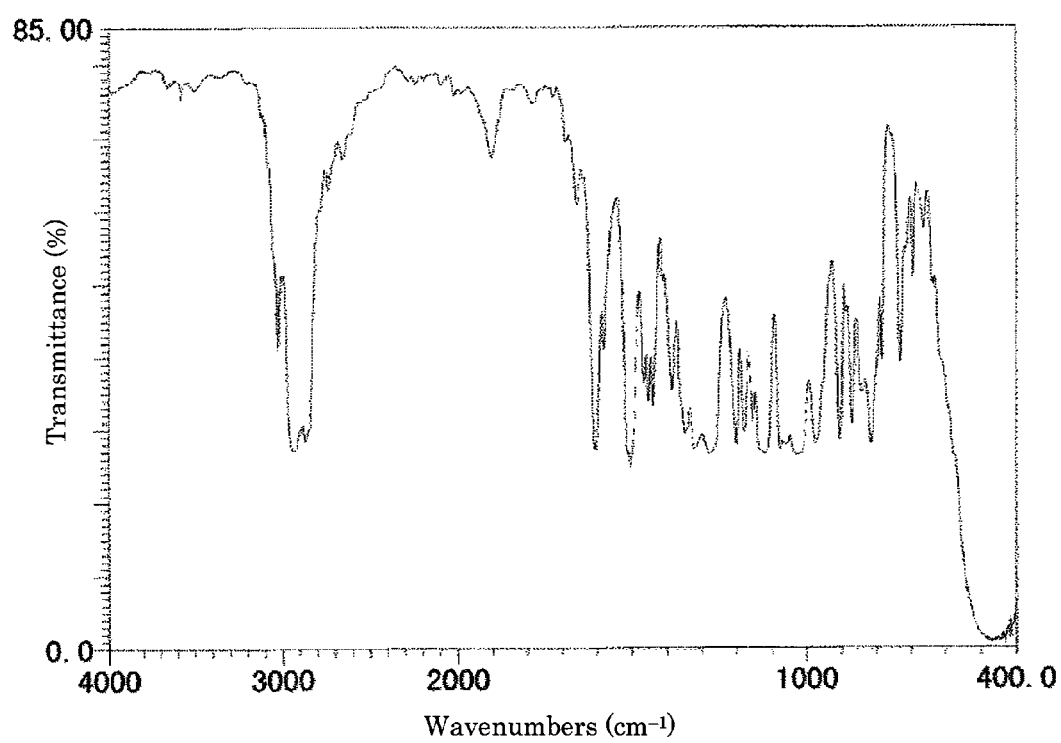
FIG. 4 is a diagram showing an infrared absorption spectrum of a compound obtained in Synthesis Example 4 (KBr tablet method), where the horizontal axis denotes wavenumbers (cm$^{-1}$), and the vertical axis denotes transmittance (%).

A diagram showing an infrared absorption spectrum of the tetrahydropyranyl compound obtained in Synthesis Example 4 (KBr tablet method) is in FIG. 4.

Synthesis Example 5 (Synthesis of an Intermediate for a Tetrahydropyranyl Compound Shown as an Example)

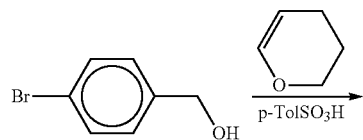

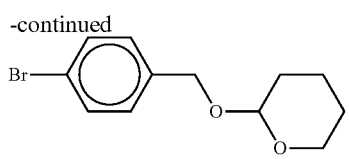

In a four-necked flask, 50.43 g of 4-bromobenzyl alcohol, 45.35 g of 3,4-dihydro-2H-pyran and 150 mL of tetrahydrofuran were placed.

The ingredients were stirred at 5° C., and 0.512 g of p-toluenesulfonic acid was poured. Stirring was continued for 2 hours at room temperature.

An extracting process with ethyl acetate, a dehydrating process with magnesium sulfate, and an adsorbing process with activated clay and silica gel were performed.

By filtrating, washing and concentrating the ingredients, an intended product was thus obtained (yield: 72.50 g, colorless oily matter).

Figure 5:
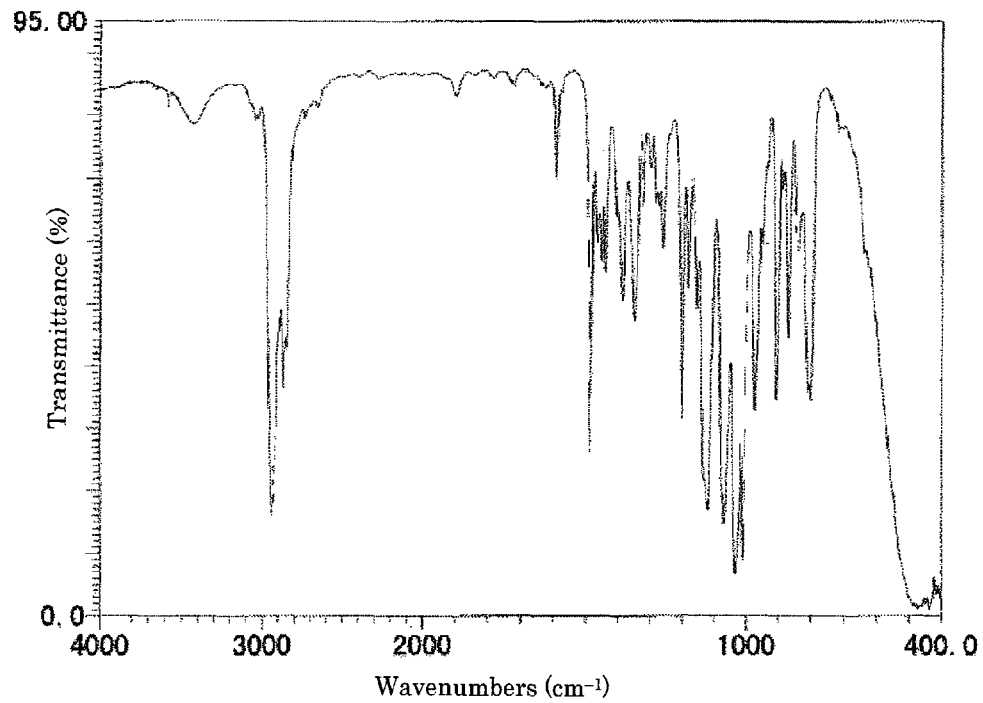
FIG. 5 is a diagram showing an infrared absorption spectrum of a compound obtained in Synthesis Example 5 (KBr tablet method), where the horizontal axis denotes wavenumbers (cm$^{-1}$), and the vertical axis denotes transmittance (%).

A diagram showing an infrared absorption spectrum of the compound obtained in Synthesis Example 5 (KBr tablet method) is in FIG. 5.

Example 2

Synthesis Example 6 (Example 2: Synthesis of a Tetrahydropyranyl Compound No. 2 Shown as an Example)

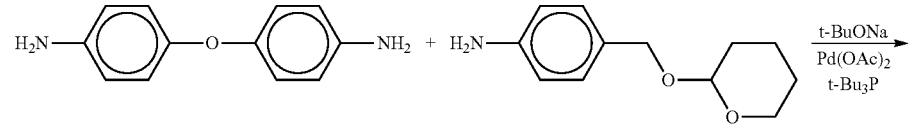

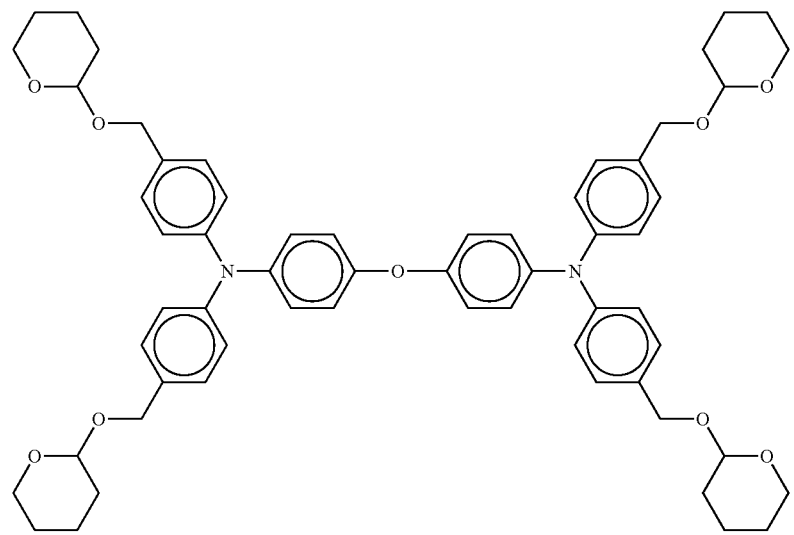

In a four-necked flask, 3.0 g of 4,4'-diaminodiphenyl ether, 17.896 g of the compound obtained in Synthesis Example 5, 0.336 g of palladium acetate, 13.83 g of tert-butoxysodium and 100 mL of o-xylene were placed.

In an argon gas atmosphere, the above ingredients were stirred at room temperature.

Dropwise addition of 1.214 g of tri-tert-butylphosphine was carried out.

Stirring was continued for 1 hour at 80° C. and 1 hour in a state of reflux.

The ingredients were diluted with toluene, which was followed by addition of magnesium sulfate, activated clay and silica gel, and then stirring was carried out.

The ingredients were filtered, washed and concentrated to obtain yellow oily matter.

A column cleanup with silica gel (toluene/ethyl acetate=7/3) was performed so as to effect isolation, and an intended product was thus obtained (yield: 5.7 g, pale yellow oily matter).

Figure 6:
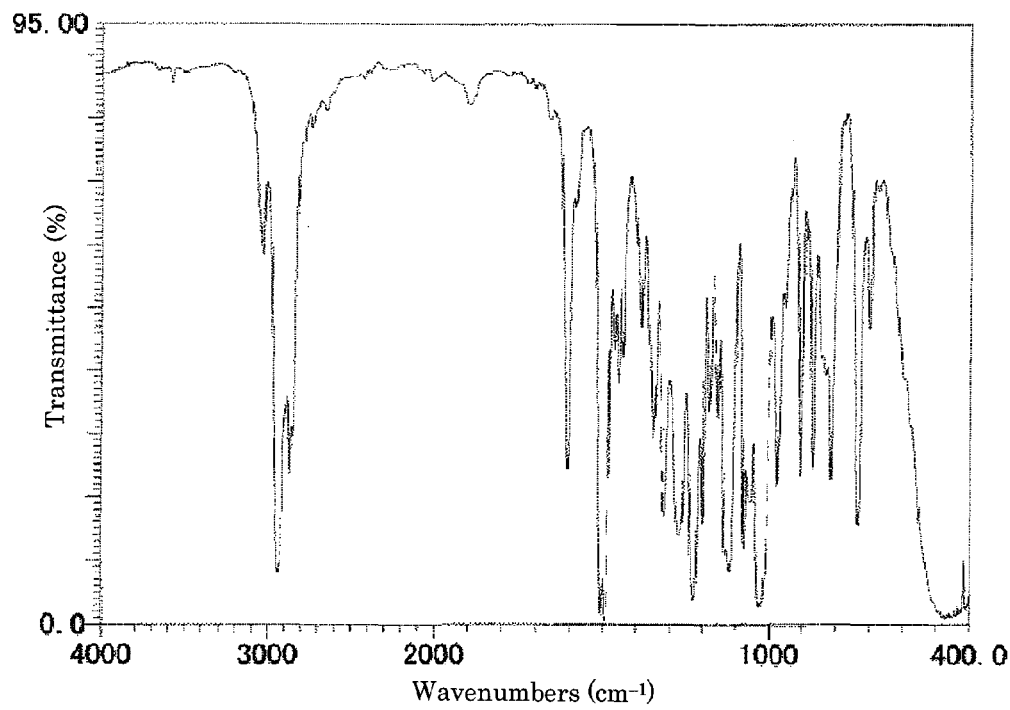
FIG. 6 is a diagram showing an infrared absorption spectrum of a compound obtained in Synthesis Example 6 (KBr tablet method), where the horizontal axis denotes wavenumbers (cm$^{-1}$), and the vertical axis denotes transmittance (%).

A diagram showing an infrared absorption spectrum of the compound obtained in Synthesis Example 6 (KBr tablet method) is in FIG. 6.

Example 3

Synthesis Example 7 (Example 3: Synthesis of a Tetrahydropyranyl Compound No. 3 Shown as an Example)

In a four-necked flask, 3.18 g of 4,4'-ethylenedianiline, 17.896 g of the compound obtained in Synthesis Example 5, 0.336 g of palladium acetate, 13.83 g of tert-butoxysodium and 100 mL of o-xylene were placed.

In an argon gas atmosphere, the above ingredients were stirred at room temperature.

Dropwise addition of 1.214 g of tri-tert-butylphosphine was carried out.

Stirring was continued for 1 hour at 80° C. and 1 hour in a state of reflux.

The ingredients were diluted with toluene, which was followed by addition of magnesium sulfate, activated clay and silica gel, and then stirring was carried out.

The ingredients were filtered, washed and concentrated to obtain yellow oily matter.

A column cleanup with silica gel (toluene/ethyl acetate=4/1) was performed so as to effect isolation, and an intended product was thus obtained (yield: 5.7 g, pale yellow oily matter).

Figure 7:
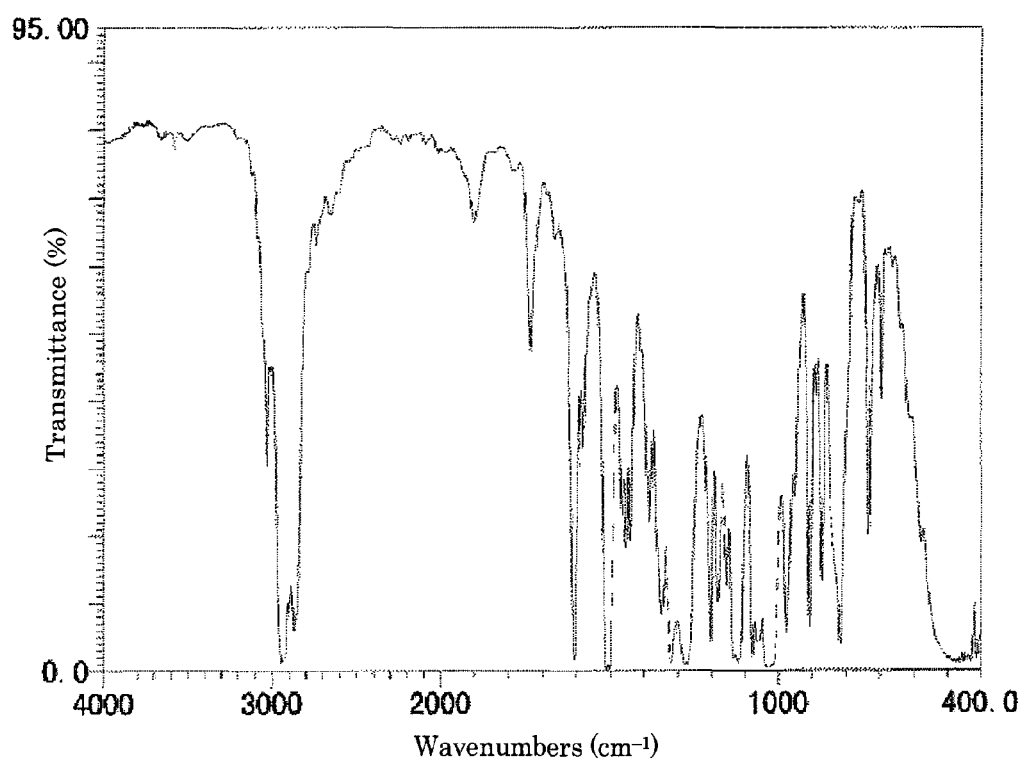
FIG. 7 is a diagram showing an infrared absorption spectrum of a compound obtained in Synthesis Example 7 (KBr tablet method), where the horizontal axis denotes wavenumbers (cm$^{-1}$), and the vertical axis denotes transmittance (%).

A diagram showing an infrared absorption spectrum of the compound obtained in Synthesis Example 7 (KBr tablet method) is in FIG. 7.

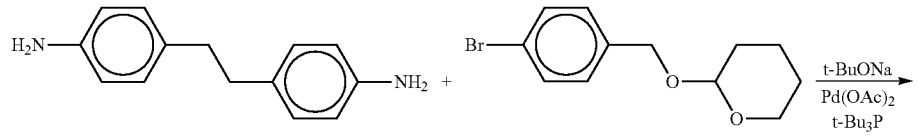

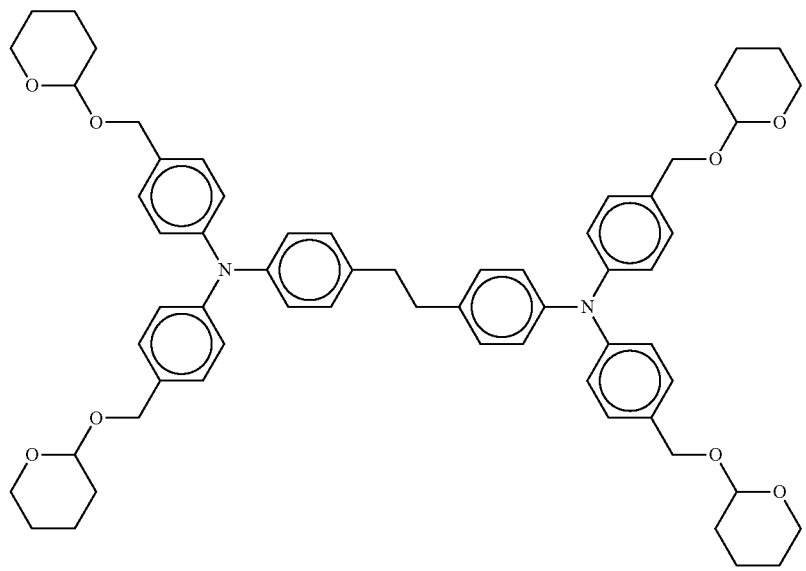

Example 4

Synthesis Example 8 (Example 4: Synthesis of a Tetrahydropyranyl Compound No. 4 Shown as an Example)

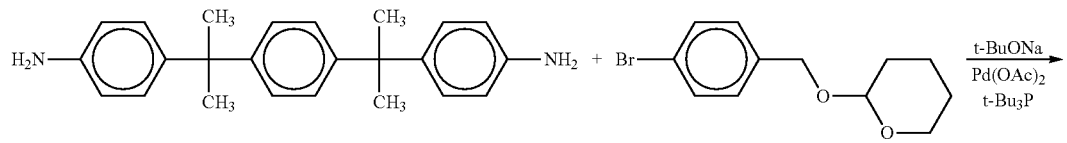

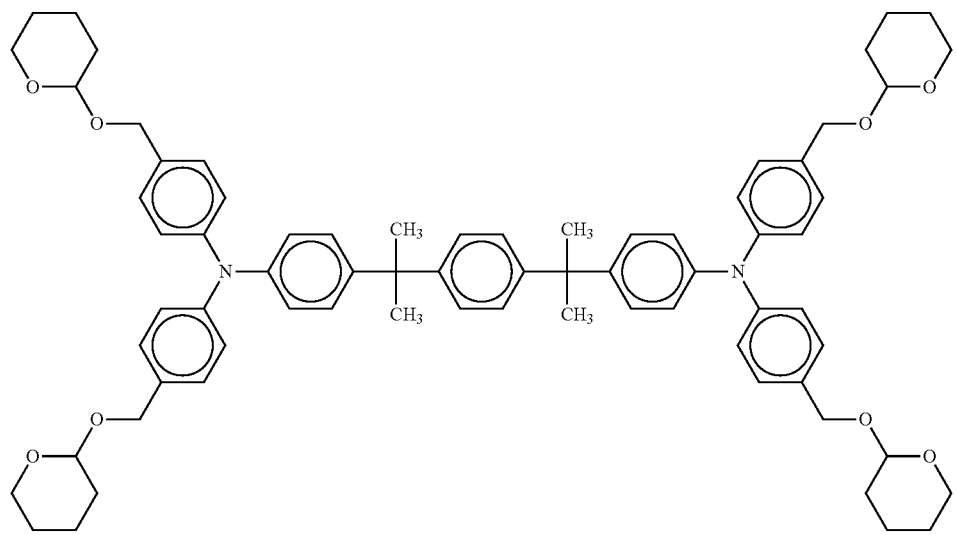

In a four-necked flask, 10.335 g of α,α'-bis(4-aminophenyl)-1,4-diisopropylbenzene, 39.05 g of the compound obtained in Synthesis Example 5, 0.673 g of palladium acetate, 27.677 g of tert-butoxysodium and 200 mL of o-xylene were placed.

In an argon gas atmosphere, the above ingredients were stirred at room temperature.

Dropwise addition of 2.43 g of tri-tert-butylphosphine was carried out.

Stirring was continued for 1 hour at 80° C. and 2 hours in a state of reflux.

The ingredients were diluted with toluene, which was followed by addition of magnesium sulfate, activated clay and silica gel, and then stirring was carried out.

The ingredients were filtered, washed and concentrated to obtain yellow oily matter.

A column cleanup with silica gel (toluene/ethyl acetate=4/1) was performed so as to effect isolation, and an intended product was thus obtained (yield: 23.5 g, yellow oily matter).

Figure 8:
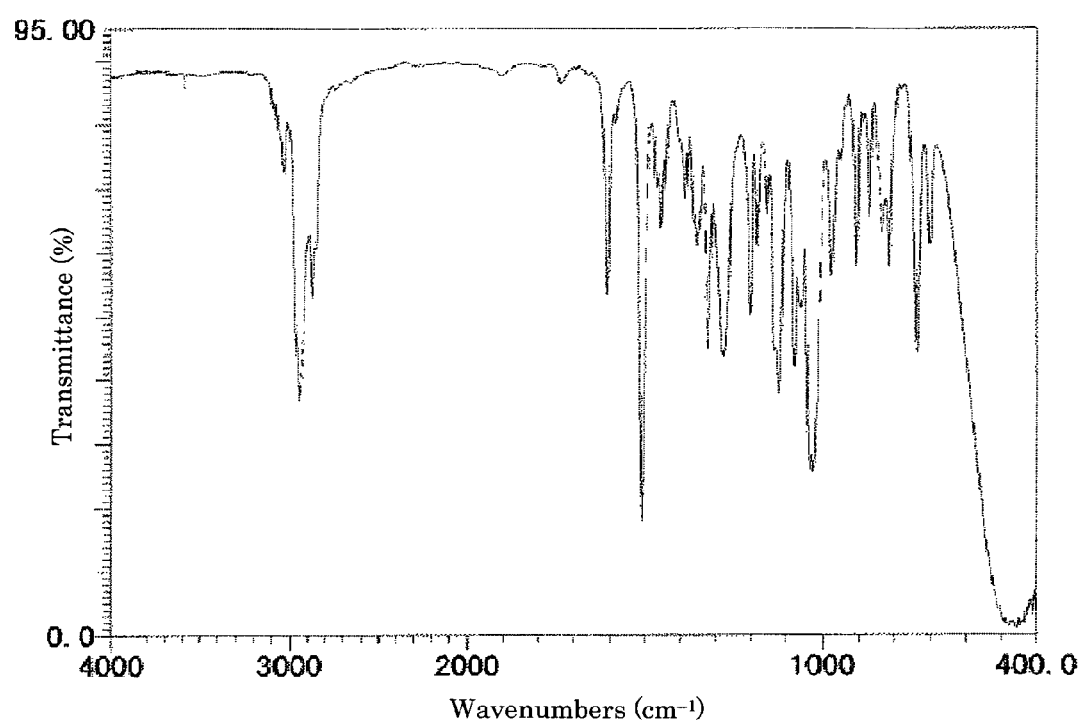
FIG. 8 is a diagram showing an infrared absorption spectrum of a compound obtained in Synthesis Example 8 (KBr tablet method), where the horizontal axis denotes wavenumbers (cm$^{-1}$), and the vertical axis denotes transmittance (%).

A diagram showing an infrared absorption spectrum of the compound obtained in Synthesis Example 8 (KBr tablet method) is in FIG. 8.

Example 5

Synthesis Example 9 (Example 5: Synthesis of a Tetrahydropyranyl Compound No. 5 Shown as an Example)

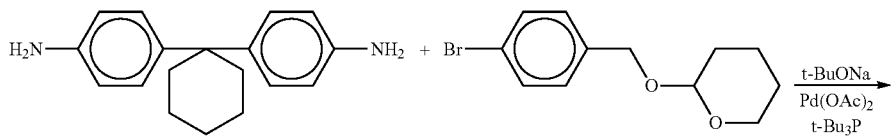

-continued

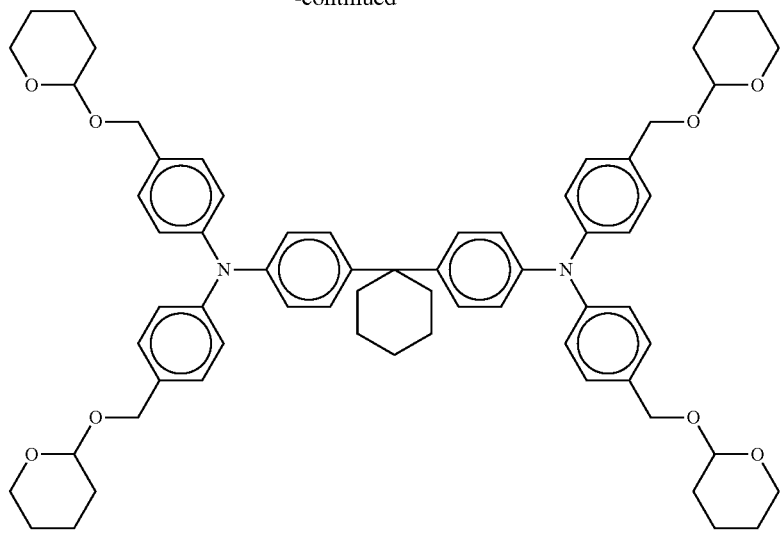

In a four-necked flask, 9.323 g of 1,1-bis(4-aminophenyl)cyclohexene, 45.55 g of the compound obtained in Synthesis Example 5, 0.785 g of palladium acetate, 32.289 g of tert-butoxysodium and 300 mL of o-xylene were placed.

In an argon gas atmosphere, the above ingredients were stirred at room temperature.

Dropwise addition of 2.43 g of tri-tert-butylphosphine was carried out.

Stirring was continued for 1 hour at 80° C. and 2 hours in a state of reflux.

The ingredients were diluted with toluene, which was followed by addition of magnesium sulfate, activated clay and silica gel, and then stirring was carried out.

The ingredients were filtered, washed and concentrated to obtain yellow oily matter.

A column cleanup with silica gel (toluene/ethyl acetate=5/1) was performed so as to effect isolation, and an intended product was thus obtained (yield: 11.42 g, yellow amorphous product).

Figure 9:
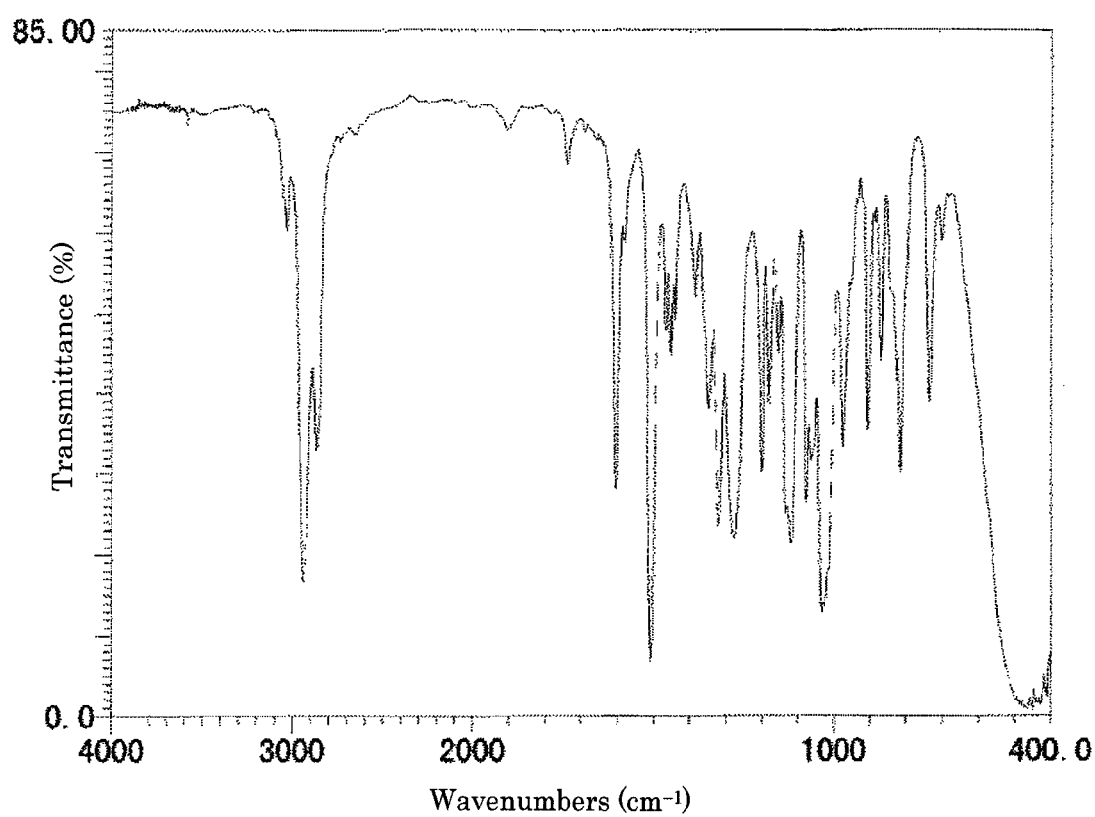
FIG. 9 is a diagram showing an infrared absorption spectrum of a compound obtained in Synthesis Example 9 (KBr tablet method), where the horizontal axis denotes wavenumbers (cm$^{-1}$), and the vertical axis denotes transmittance (%).

A diagram showing an infrared absorption spectrum of the compound obtained in Synthesis Example 9 (KBr tablet method) is in FIG. 9.

It was found that a tetrahydropyranyl compound of the present invention, represented by General Formula (1) or (6) above, can be produced with ease by reacting together a methylol compound represented by General Formula (2) or (7) above, as synthesized by the above reaction, and 3,4-dihydro-2H-pyran represented by General Formula (3) above.

Also, it was found that a tetrahydropyranyl compound of the present invention, represented by General Formula (1) or (6) above, can be produced with ease by reacting together an amine compound represented by General Formula (4) or (8) above and a bromo compound represented by General Formula (5) or (9) above. Further, the above-mentioned other tetrahydropyranyl compounds Nos. 6 to 15 shown as examples can also be produced with ease by the foregoing reactions.

Example 6

<Evaluation of Charge Transporting Property>

Application Example 1

A coating liquid for an underlying layer, a coating liquid for a charge generation layer, and a coating liquid for a charge transport layer, which had the compositions below, were sequentially applied over an aluminum plate and dried to form an underlying layer (0.3 μm in thickness), a charge generation layer (0.3 μm in thickness) and a charge transport layer (20 μm in thickness) respectively. In this manner, five photoconductors Nos. 1 to 5 were produced.

The five photoconductors were produced respectively using the tetrahydropyranyl compounds synthesized in Synthesis Examples as components of the coating liquids for charge transport layers; the photoconductor No. 1 was produced using the tetrahydropyranyl compound No. 1.

<Coating Liquid for Underlying Layer>

| | |
|---|---|
| Polyamide resin (CM-8000, manufactured by Toray Industries, Inc.) | 2 parts |
| Methanol | 49 parts |
| butanol | 49 parts |

<Coating Liquid for Charge Generation Layer>

Bisazo pigment represented by the structural formula below

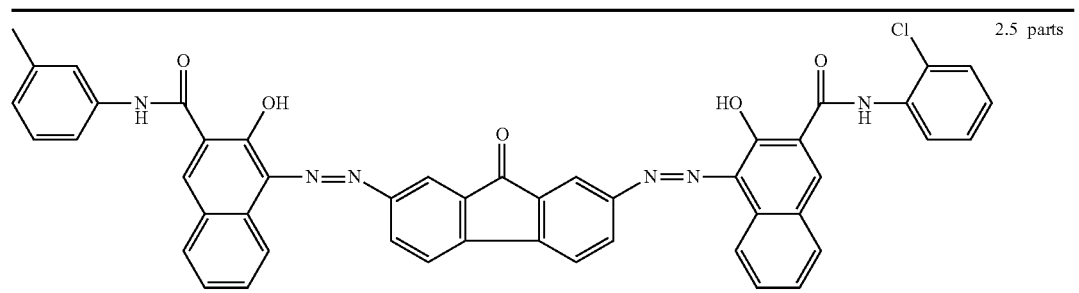

| | |
|---|---:|
| Polyvinyl butyral (XYHL, manufactured by Union Carbide Corporation) | 0.5 parts |
| Cyclohexanone | 200 parts |
| Methyl ethyl ketone | 80 parts |

<Coating Liquid for Charge Transport Layer>

| | |
|---|---:|
| Bisphenol Z polycarbonate (PANLITE TS-2050, manufactured by Teijin Chemicals Ltd.) | 10 parts |
| Charge transporting compound (tetrahydropyranyl compound No. 1) | 10 parts |
| Tetrahydrofuran | 80 parts |
| Tetrahydrofuran solution of 1% silicone oil (KF-50-100CS, manufactured by Shin-Etsu Chemical Co., Ltd.) | 0.2 parts |

Example 7

Application Example 2

A photoconductor, named "photoconductor No. 2", was produced in the same manner as in Example 6 (Application Example 1) except that the tetrahydropyranyl compound No. 2 was used instead of the tetrahydropyranyl compound No. 1.

Example 8

Application Example 3

A photoconductor, named "photoconductor No. 3", was produced in the same manner as in Example 6 (Application Example 1) except that the tetrahydropyranyl compound No. 3 was used instead of the tetrahydropyranyl compound No. 1.

Example 9

Application Example 4

A photoconductor, named "photoconductor No. 4", was produced in the same manner as in Example 6 (Application Example 1) except that the tetrahydropyranyl compound No. 4 was used instead of the tetrahydropyranyl compound No. 1.

Example 10

Application Example 5

A photoconductor, named "photoconductor No. 5", was produced in the same manner as in Example 6 (Application Example 1) except that the tetrahydropyranyl compound No. 5 was used instead of the tetrahydropyranyl compound No. 1.

Comparative Example 1

A photoconductor, named "photoconductor No. 6", was produced in the same manner as in Example 6 (Application Example 1) except that the compound (I) shown below was used instead of the tetrahydropyranyl compound No. 1.

Compound (I)

Comparative Example 2

A photoconductor, named "photoconductor No. 7", was produced in the same manner as in Example 6 (Application Example 1) except that the compound (II) shown below was used instead of the tetrahydropyranyl compound No. 1.

Compound (II)

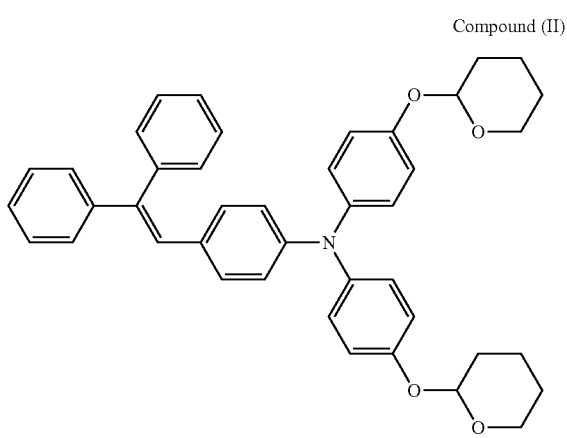 [SMILES: C(=C(c1ccccc1)c1ccccc1)c1ccc(N(c2ccc(OC3CCCCO3)cc2)c2ccc(OC3CCCCO3)cc2)cc1]

Using a commercially available electrostatic copying paper tester (EPA-8200, manufactured by Kawaguchi Electric Works Co., Ltd.), charge transporting properties of the photoconductors Nos. 1 to 7 obtained as described above were evaluated based upon half decay exposure and residual potential.

Specifically, in a dark place, each photoconductor was charged to −800 V by corona discharge of −6 kV; thereafter, tungsten lamp light was applied such that the illuminance at the photoconductor surface became 4.5 lux, the length of time (second) spent until the potential became ½ times as great was measured, and the half decay exposure E1/2(lux·sec) was calculated.

Also, the residual potential (−V) at the time when 30 seconds had passed after the exposure was measured. Note that the smaller the half decay exposure is, the greater sensitivity can be yielded, and that the smaller the residual potential is, the smaller the trapped charge is.

The results of the evaluations are shown in Table 1 below.

TABLE 1

| Photo-conductor No. | Charge transporting compound | Half decay exposure E½ (lux · sec) | Residual potential (−V) |
|---|---|---|---|
| 1 | Tetrahydropyranyl compound No. 1 | 0.52 | 0 |
| 2 | Tetrahydropyranyl compound No. 2 | 0.58 | 0 |
| 3 | Tetrahydropyranyl compound No. 3 | 0.58 | 0 |
| 4 | Tetrahydropyranyl compound No. 4 | 0.61 | 0 |
| 5 | Tetrahydropyranyl compound No. 5 | 0.56 | 0 |
| 6 | Compound (I) | 0.56 | 0 |
| 7 | Compound (II) | 2.05 | 10 |

The evaluation results demonstrate that clearly the photoconductors Nos. 1 to 5 containing the respective tetrahydropyranyl compounds of the present invention were not inferior to the comparative photoconductor containing the compound (I) (which is a known material not containing a tetrahydropyranyl group) and had small half decay exposure, favorable sensitivity, no residual potential and no trapped charge, thereby exhibiting a favorable charge transporting property.

Also, during long-term use, the low crystallinity of the charge transport materials themselves yielded superiority in terms of stability of the liquids for coating films.

The invention claimed is:

1. A tetrahydropyranyl compound represented by Formula (1):

Formula (1)

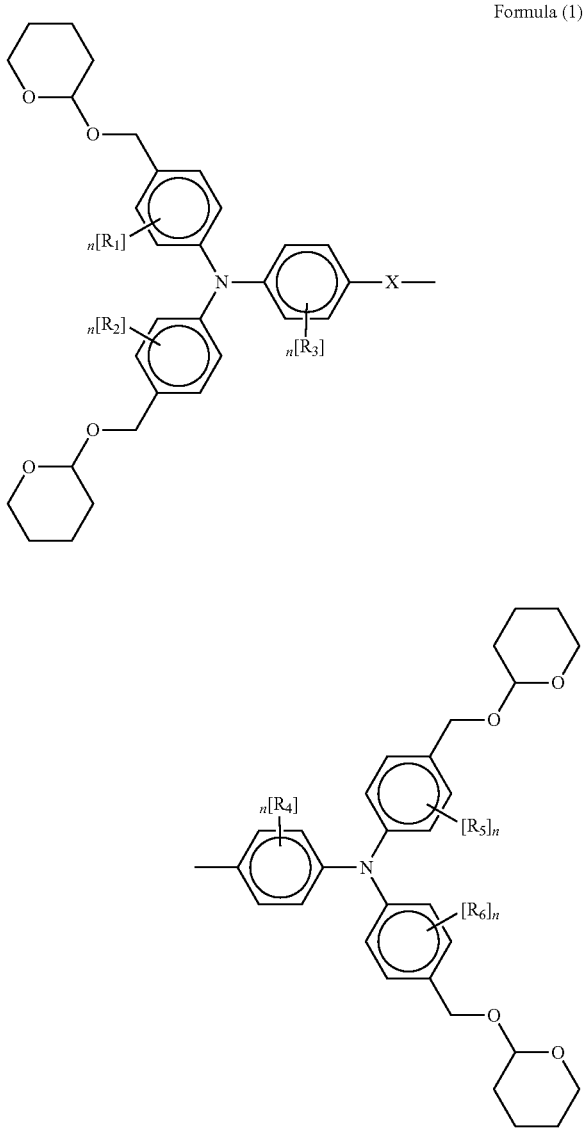

where X is —O—, —CH—, —CH$_2$CH$_2$—, —C(CH$_3$)$_2$—C$_6$H$_4$—C(CH$_3$)$_2$— or —C(CH$_3$)$_2$—; R$_1$, R$_2$, R$_3$, R$_4$, R$_5$ and R$_6$ each independently are selected from the group consisting of a hydrogen atom, a methyl group and an ethyl group; and n is an integer of 1 to 4.

2. A method for producing a tetrahydropyranyl compound represented by Formula (1), the method comprising:

reacting a methylol compound represented by Formula (2) with 3,4-dihydro-2H-pyran represented by Formula (3):

Formula (2)

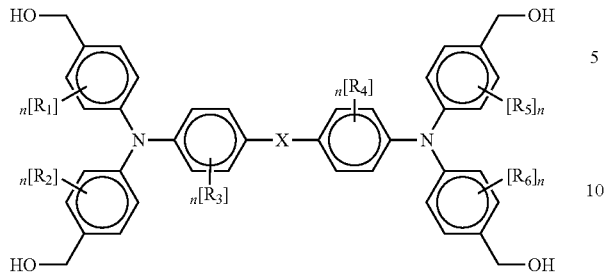

where X is —O—, —CH₂, —CH₂CH₂—, —C(CH₃)₂—C₆H₄—C(CH₃)₂— or —C(CH₃)₂; $R_1$, $R_2$, $R_3$, $R_4$, $R_5$ and $R_6$ each independently are selected from the group consisting of a hydrogen atom, a methyl group and an ethyl group; and n is an integer of 1 to 4, Formula (3)

Formula (1)

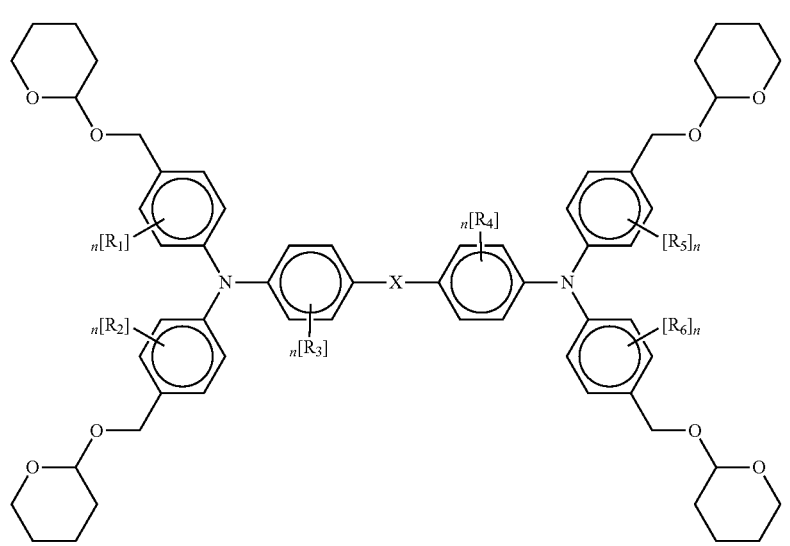

where X is —O—, —CH₂—, —CH₂CH₂—, —C(CH₃)₂—C₆H₄—C(CH₃)₂— or —C(CH₃)₂—; $R_1$, $R_2$, $R_3$, $R_4$, $R_5$ and $R_6$ each independently are selected from the group consisting of a hydrogen atom, a methyl group and an ethyl group; and n is an integer of 1 to 4.

3. A method for producing a tetrahydropyranyl compound represented by Formula (1), comprising:
reacting an amine compound represented by Formula (4) with a bromo compound represented by Formula (5):

Formula (4)

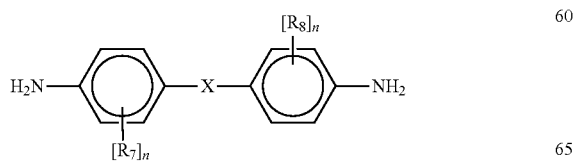

where X is —O—, —CH$_2$—, —CH$_2$CH$_2$—, —C(CH$_3$)$_2$—C$_6$H$_4$—C(CH$_3$)$_2$ or —C(CH$_3$)$_2$—; R$_7$ and R$_8$ each independently are selected from the group consisting of a hydrogen atom, a methyl group and an ethyl group; and n is an integer of 1 to 4, Formula (5)

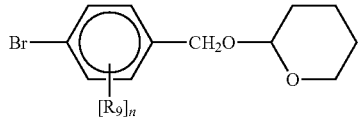

where R$_9$ is a hydrogen atom, a methyl group or an ethyl group, and n is an integer of 1 to 4, Formula (1)

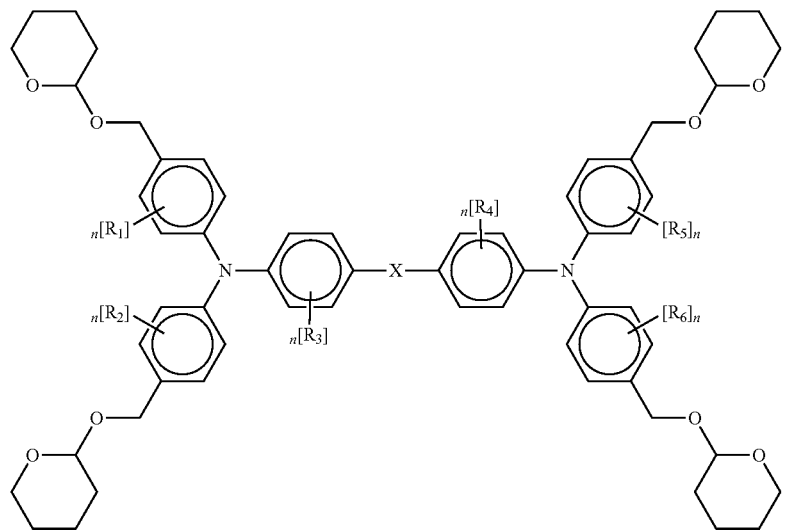

where X is —O—, —CH$_2$—, —CH$_2$CH$_2$—, —C(CH$_3$)—C$_6$H$_4$—C(CH$_3$)$_2$— or —C(CH$_3$)$_2$—; R$_1$, R$_2$, R$_3$, R$_4$, R$_5$ and R$_6$ each independently are selected from the group consisting of a hydrogen atom, a methyl group and an ethyl group; and n is an integer of 1 to 4.

4. The tetrahydropyranyl compound according to claim 1, having Formula (6):

Formula (6)

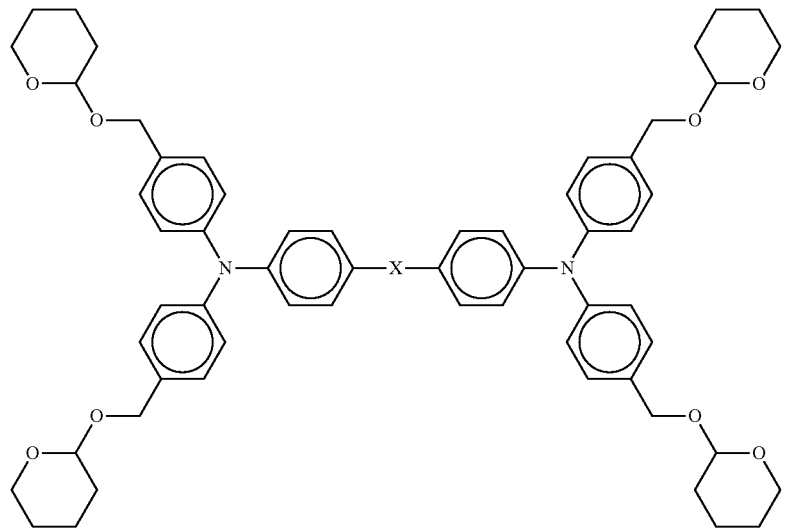

where X is —O—, —CH$_2$—, —CH$_2$CH$_2$—, —C(CH$_3$)$_2$—C$_6$H$_4$—C(CH$_3$)$_2$— or —C(CH$_3$)$_2$—.

5. The tetrahydropyranyl compound of claim 4, wherein X is —O— in Formula (6).

6. The tetrahydropyranyl compound of claim 4, wherein X is —CH$_2$— in Formula (6).

7. The tetrahydropyranyl compound of claim 4, wherein X is —CH$_2$CH$_2$— in Formula (6).

8. The tetrahydropyranyl compound of claim 4, wherein X is —C(CH$_3$)$_2$—C$_6$H$_4$—C(CH$_3$)$_2$— in Formula (6).

9. The tetrahydropyranyl compound of claim 4, wherein X is —C(CH$_3$)$_2$— in Formula (6).

10. The method of claim 1, wherein every R$_1$, R$_2$, R$_3$, R$_4$, R$_5$ and R$_6$ in Formulae (1) and (2) is a hydrogen atom.

11. The method of claim 3, wherein:

every R$_1$, R$_2$, R$_3$, R$_4$, R$_5$ and R$_6$ in Formula (1) is a hydrogen atom;

every R$_7$ and R$_8$ in Formula (4) is a hydrogen atom; and every R$_9$ in Formula (5) is a hydrogen atom.

12. The method of claim 2, wherein X is —O— in Formulae (1) and (2).

13. The method of claim 2, wherein X is —CH$_2$— in Formulae (1) and (2).

14. The method of claim 2, wherein X is —CH$_2$CH$_2$— in Formulae (1) and (2).

15. The method of claim 2, wherein X is —C(CH$_3$)$_2$—C$_6$H$_4$—C(CH$_3$)$_2$— in Formulae (1) and (2).

16. The method of claim 3, wherein X is —O— in Formulae (1) and (4).

17. The method of claim 3, wherein X is —CH$_2$— in Formulae (1) and (4).

18. The method of claim 3, wherein X is —CH$_2$CH$_2$— in Formulae (1) and (4).

19. The method of claim 3, wherein X is —C(CH$_3$)$_2$—C$_6$H$_4$—C(CH$_3$)$_2$— in Formulae (1) and (4).

* * * * *